(12) United States Patent
Theofilos

(10) Patent No.: US 11,786,277 B2
(45) Date of Patent: Oct. 17, 2023

(54) TOWER PEDICLE SCREW SYSTEM

(71) Applicant: SNJ Patents, LLC, Palm Beach Gardens, FL (US)

(72) Inventor: Charles Theofilos, Palm Beach Gardens, FL (US)

(73) Assignee: SNJ Patents, LLC, Palm Beach Gardens, FL (US)

( * ) Notice: Subject to any disclaimer, the term of this patent is extended or adjusted under 35 U.S.C. 154(b) by 0 days.

(21) Appl. No.: 17/400,885

(22) Filed: Aug. 12, 2021

(65) Prior Publication Data

US 2022/0047305 A1 Feb. 17, 2022

Related U.S. Application Data

(60) Provisional application No. 63/064,723, filed on Aug. 12, 2020.

(51) Int. Cl.
*A61B 17/70* (2006.01)

(52) U.S. Cl.
CPC ........ *A61B 17/708* (2013.01); *A61B 17/7032* (2013.01)

(58) Field of Classification Search
CPC .............. A61B 17/708; A61B 17/7079; A61B 17/7077; A61B 17/7083; A61B 17/7085; A61B 17/7086; A61B 17/7088; A61B 17/7089; A61B 17/7076
See application file for complete search history.

(56) References Cited

U.S. PATENT DOCUMENTS

| | | | | |
|---|---|---|---|---|
| 5,534,001 A | * | 7/1996 | Schlapfer | A61B 17/7032 606/302 |
| 2009/0222046 A1 | * | 9/2009 | Gorek | A61B 17/7085 606/279 |
| 2010/0198271 A1 | * | 8/2010 | Leone | A61B 17/7076 606/301 |
| 2014/0052187 A1 | * | 2/2014 | McBride | A61B 17/7085 606/264 |
| 2015/0359571 A1 | * | 12/2015 | Biedermann | A61B 17/7032 606/246 |
| 2018/0098799 A1 | * | 4/2018 | Songer | A61B 17/7083 |

* cited by examiner

*Primary Examiner* — Nicholas J Plionis
(74) *Attorney, Agent, or Firm* — McHale & Slavin, P.A.

(57) ABSTRACT

Medical devices, systems, and methods related to surgical procedures, such as spinal surgeries. The medical devices, systems, and methods utilize an orthopedic or spinal screw system tower, such as a pedicle screw tower configured to be attachable to, removable from, and re-attachable to a pedicle screw head.

20 Claims, 40 Drawing Sheets

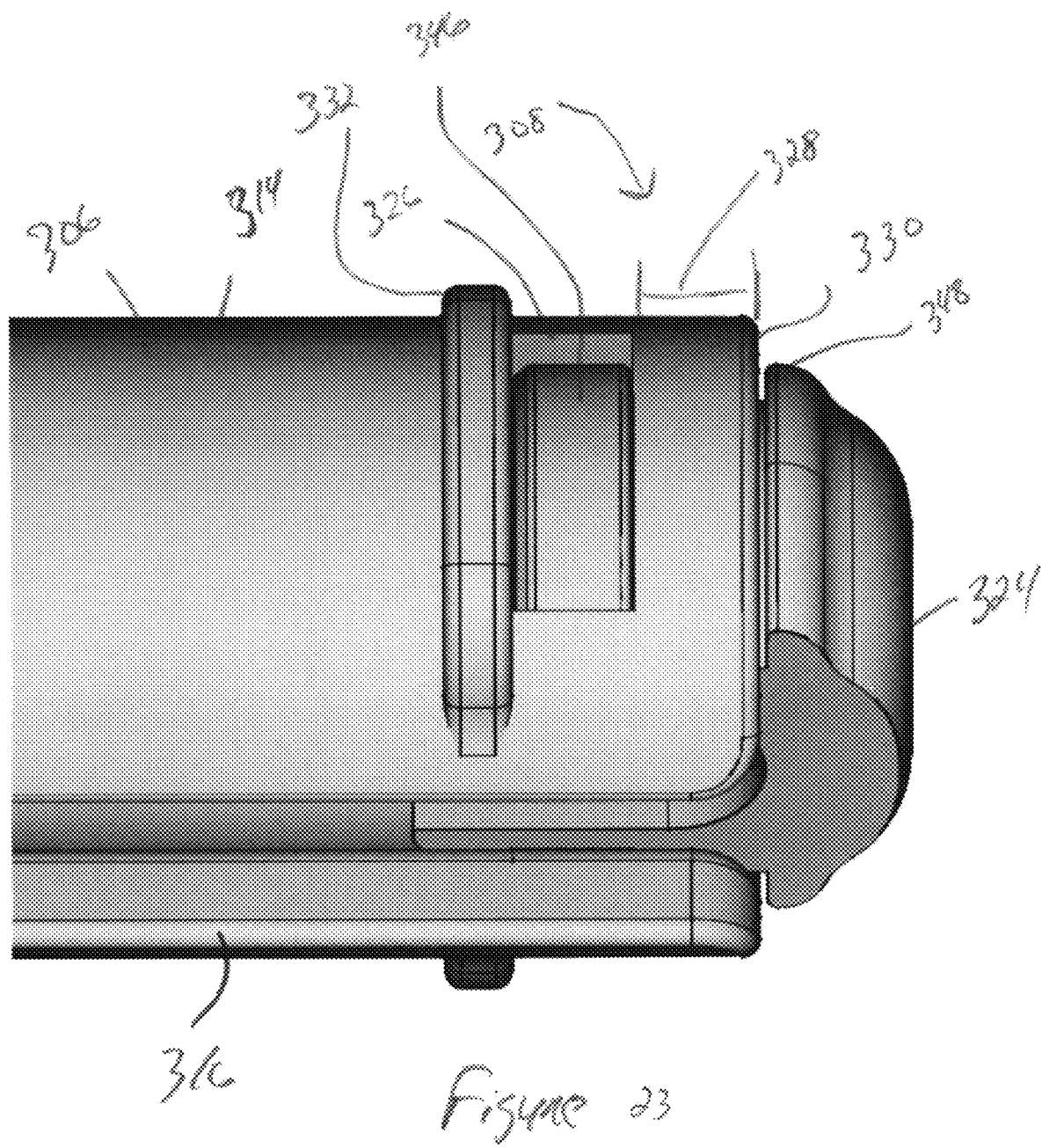

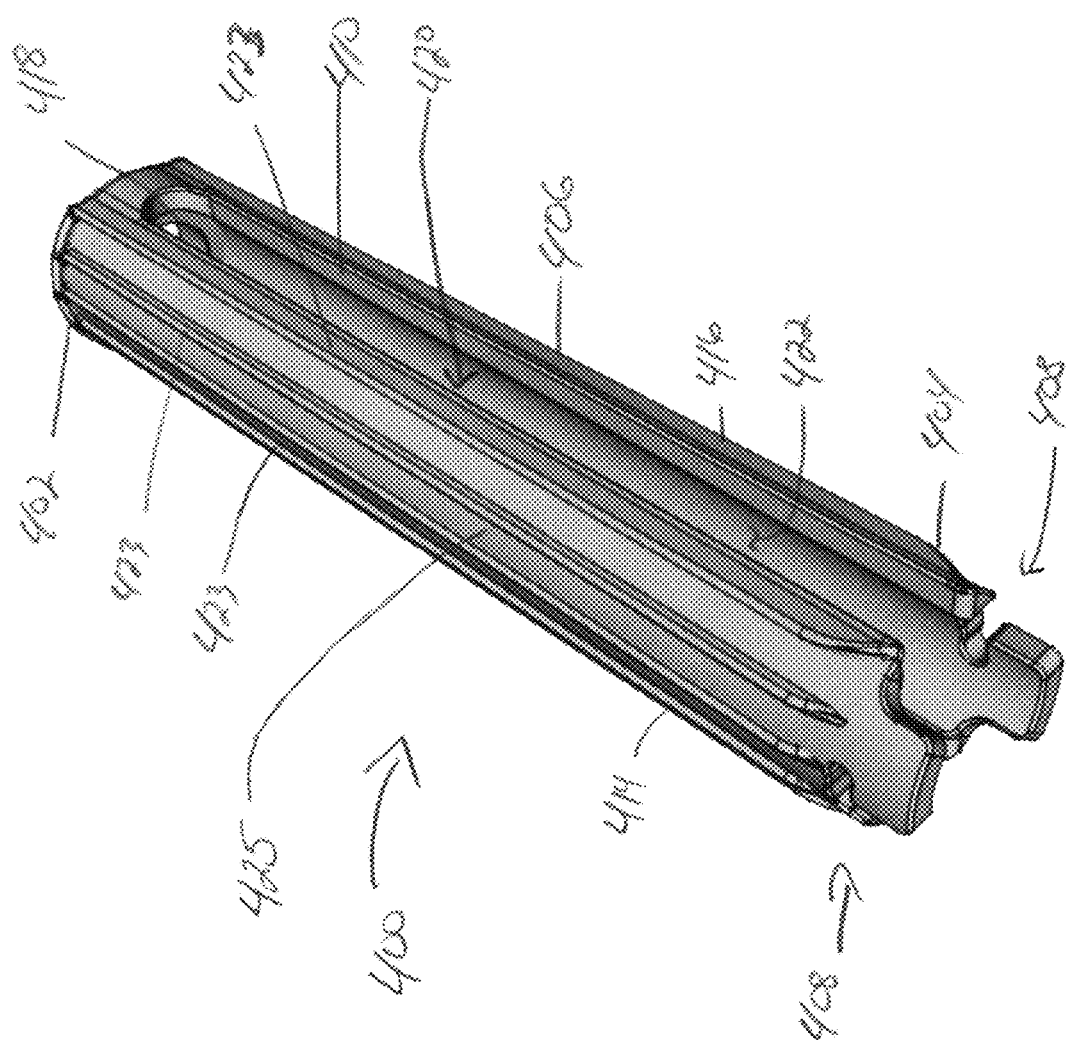

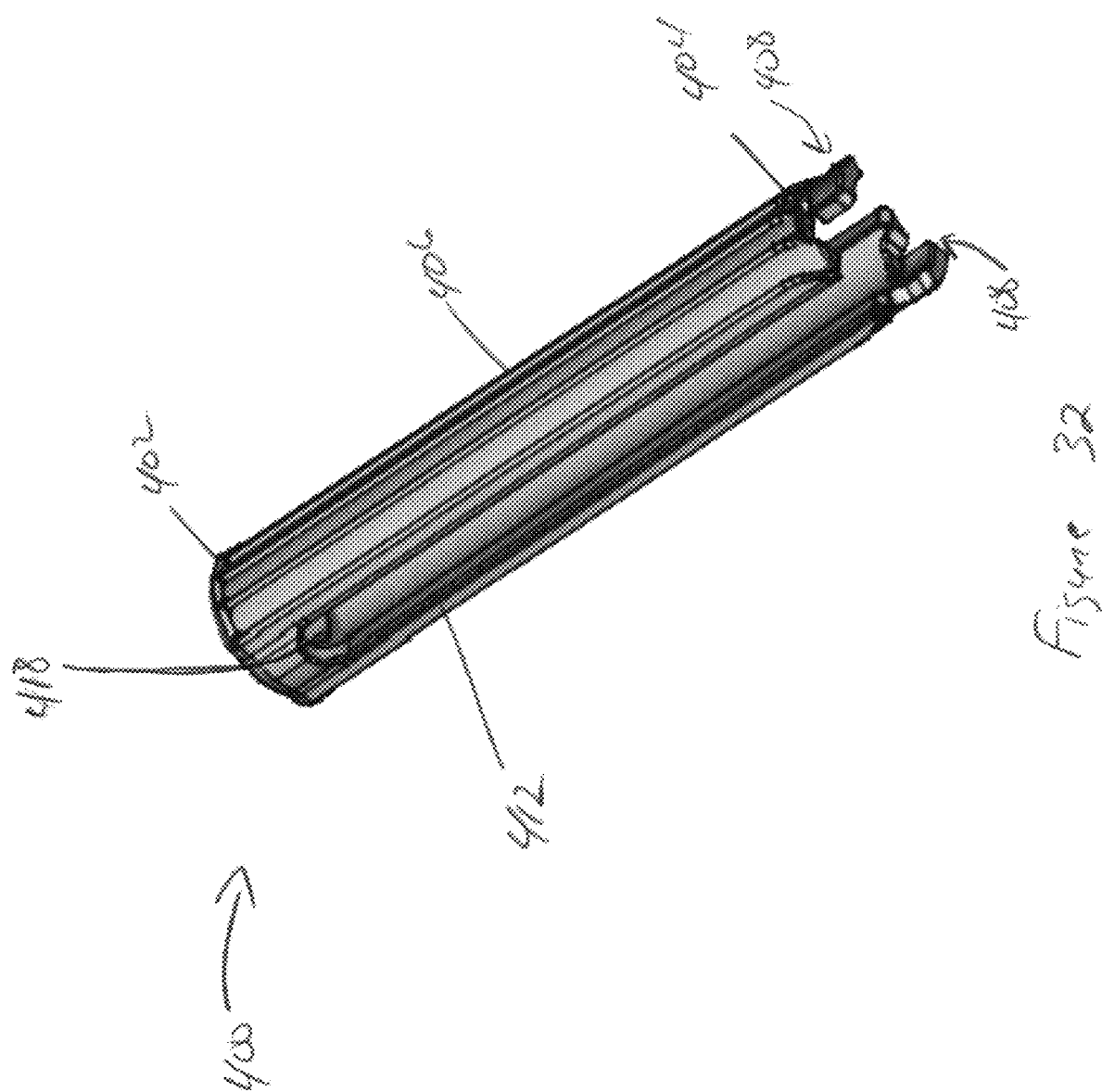

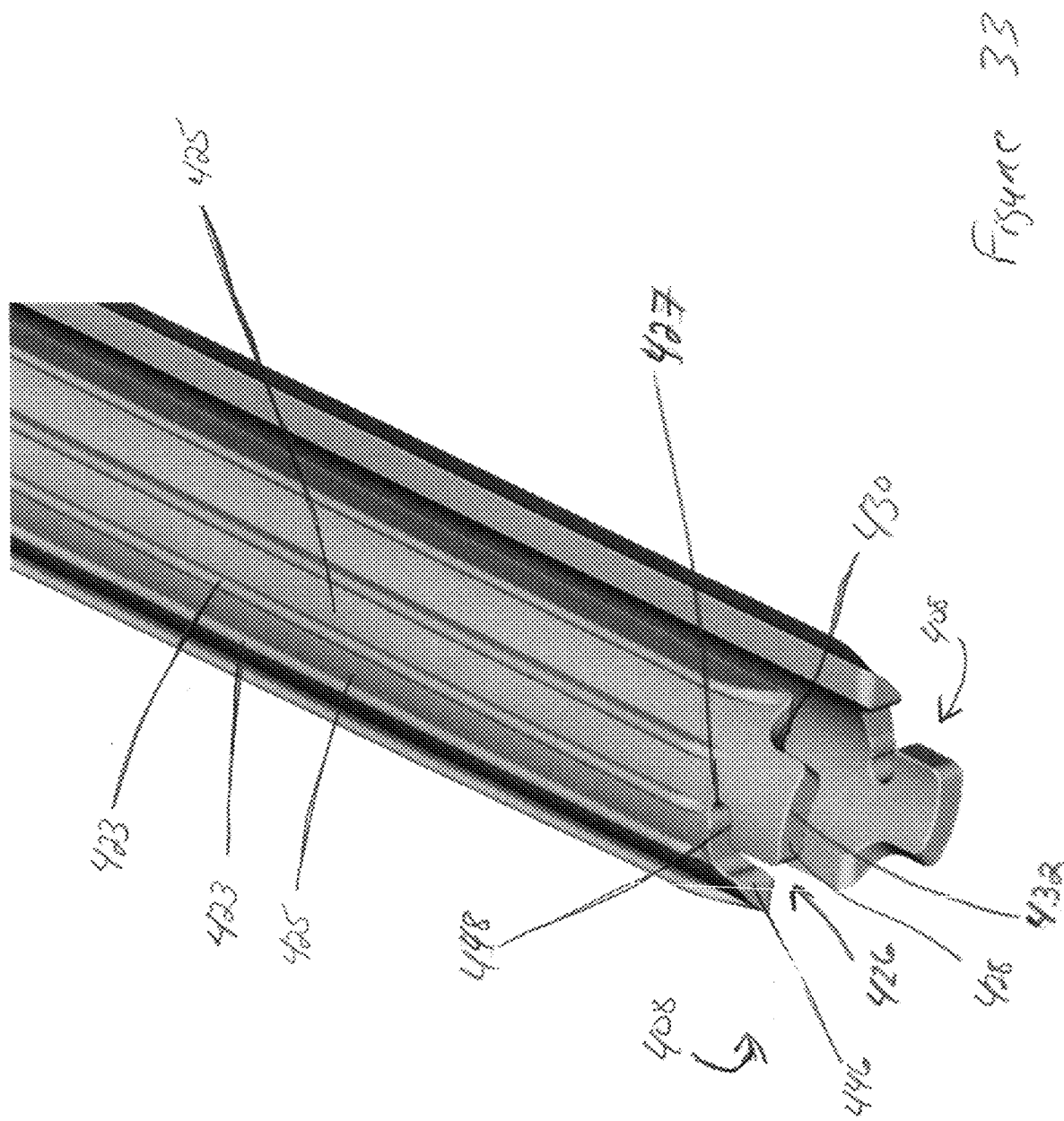

TOWER PEDICLE SCREW SYSTEM

CROSS REFERENCE TO RELATED APPLICATIONS

In accordance with 37 C.F.R. 1.76, a claim of priority is included in an Application Data Sheet filed concurrently herewith. Accordingly, the present invention claims priority to U.S. Provisional Patent Application No. 63/064,723, entitled "TOWER PEDICLE SCREW SYSTEM", filed Aug. 12, 2020. The contents of the above referenced application are incorporated herein by reference in their entirety.

FIELD OF THE INVENTION

The present invention relates to medical devices, systems, and methods; to medical devices, systems, and methods used in minimally invasive surgical procedures; to medical devices, systems, and methods related to spinal surgeries; to medical devices, systems, and methods related to the use of pedicle screws for surgical procedures such as spinal procedures; and more importantly, to medical devices, systems, and methods which provide for use of tower systems designed to allow for attachment, removal, and reattachment of the tower to a pedicle screw throughout the surgical procedure.

BACKGROUND OF THE INVENTION

Pedicle screw and lateral mass screw systems are typically utilized in spine surgery to fixate the spine, including fusion surgeries from the occipital, cervical, thoracic, lumbar, sacral/coccyx spine, and pelvis. Pedicle screws and systems are known in the art. U.S. Pat. No. 9,456,859, U.S. Patent Application Publication No. 2014/0336709, and U.S. Patent Application Publication No. 2007/0239159 are representative examples.

Pedicle screw systems may be designed with a fixed head or variable head which allows for placement in different directions. Both the fixed head and the variable head allow for the placement of a rod and set screws to be placed for fixation to multiple points throughout the spine. The variable angle head allows for easier placement and reduction of these rods into the heads by offering different angles for placement of the rods. This can pose a challenge to place the rod all the way down to the screw heads, especially in difficult cases including deformity correction and other types of spinal cases.

To aid in such techniques, pedicle screw heads can have extensions, called tabs, which help with this reduction, and can also utilize tower systems which attach to the pedicle screw heads to allow placement of the rods and aid in reduction of the rods down to the pedicle screw heads. This allows for placement of the set locking screws, which locks the rod to the pedicle screw head. The towers are usually welded onto the screw head, and can only be detached once at the end of the case. As such, the tower cannot be reattached during the surgical procedure, thus preventing the surgeon from making any changes to the system.

Accordingly, a tower system allowing for attachment, removal, and reattachment to orthopedic or spinal screw systems, such as a pedicle screw head throughout a surgical procedure, which can significantly aid in spinal surgery utilizing such systems is needed in the art.

SUMMARY OF THE INVENTION

Embodied are devices, systems, and methods for surgical procedures. Particularly, the invention is directed towards surgical devices, systems, and methods for use in spinal or other surgical procedures. The surgical devices, systems, and methods use a tower orthopedic or spinal screw system, such as a pedicle screw tower configured to be attachable to, removable from, and re-attachable to orthopedic or spinal screws or systems, such as a pedicle screw head.

It is a further objective of the invention to provide devices, systems, and methods for use in spinal or other surgical procedures.

It is yet another objective of the invention to provide devices, systems, and methods for use in surgical procedures using orthopedic or spinal screws or systems, such as pedicle screws or lateral mass screws.

It is a further objective of the invention to provide a tower orthopedic or spinal screw system;

It is yet another objective of the invention to provide a pedicle screw tower which is configured to be attachable to, removable from, and re-attachable to orthopedic or spinal systems, such as a pedicle screw head.

It is a still further objective of the invention to provide a pedicle screw head which is configured to be attachable to, removable from, and re-attachable to an orthopedic or spinal screw system tower, such as a pedicle screw tower.

It is a still further objective of the invention to teach a surgical procedure using a pedicle screw tower configured to be attachable to, removable from, and re-attachable to a pedicle screw head.

It is a further objective of the invention to teach a surgical procedure using a pedicle screw head which is configured to be attachable to, removable from, and re-attachable to a pedicle screw tower.

It is yet another objective of the invention to provide a tower pedicle screw system comprising a pedicle screw tower configured to be attachable to, removable from, and re-attachable to a pedicle screw head.

It is a still further objective of the invention to provide a tower pedicle screw system comprising a pedicle screw head which is configured to be attachable to, removable from, and re-attachable to a pedicle screw tower.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 23 illustrates a portion of the pedicle screw tower with snap fit pedicle screw locking members secured to a conjugate or keyed pedicle screw tulip head;

FIG. 26 is a side view of the snap fit tower assembly;

FIG. 31 is a perspective view of an illustrative embodiment of a turn fit tower assembly;

FIG. 32 is an alternative perspective view of the turn fit tower assembly;

FIG. 33 is a bottom perspective view of the turn fit tower assembly;

DETAILED DESCRIPTION OF THE INVENTION

Figure 1:
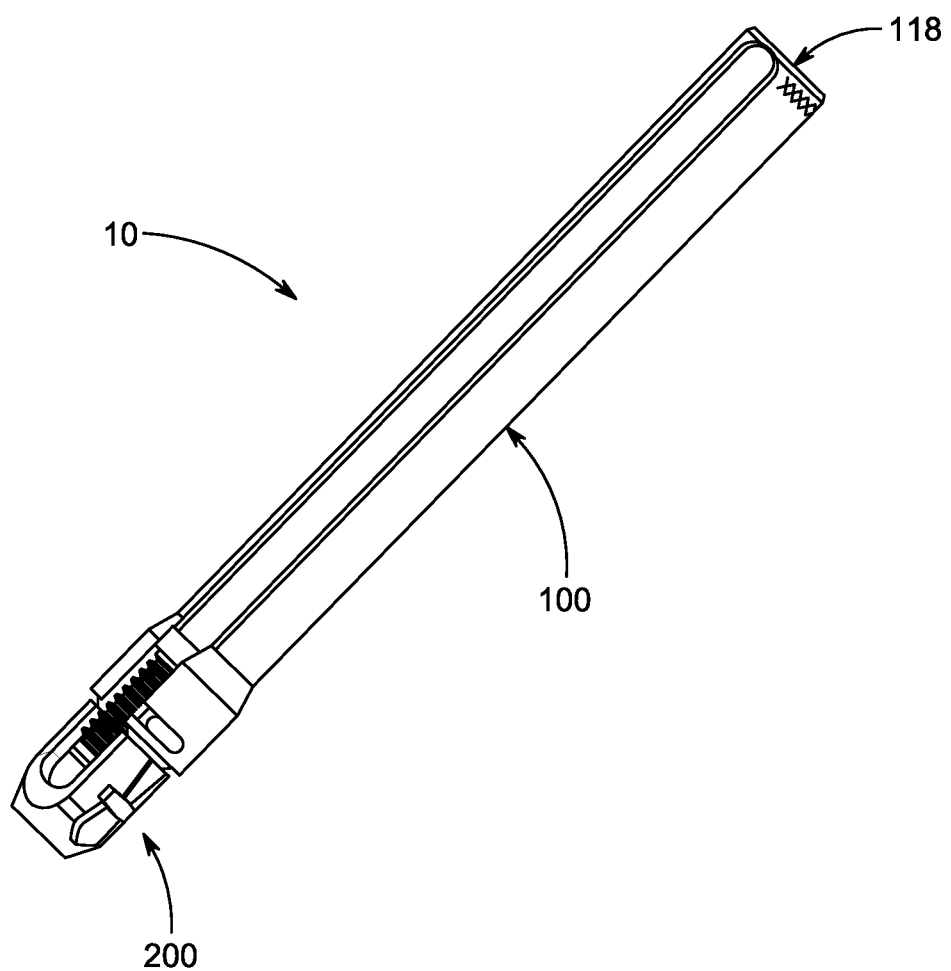
FIG. 1 is a perspective view of a tower pedicle screw system, shown with a pedicle screw head secured to a pedicle screw tower.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIG. 1, an illustrative example of a surgical system for a tower orthopedic or spinal screw system, referred to generally as a tower pedicle screw system 10 is shown. While the tower pedicle screw system 10 is referred to generally as a tower pedicle screw system and is described for use with a pedicle screw, the pedicle screw system 10 can be used in any orthopedic or spinal surgery using a tower. In addition, while the tower pedicle screw system 10 is described with application to a pedicle screw system, other systems, such as lateral mass systems or screws may be applicable. The tower pedicle screw system 10 may comprise one or both of a pedicle screw tower 100 and a pedicle screw tulip 200. The pedicle screw tower 100 is configured to be attachable to, removable from, and re-attachable to the pedicle screw tulip 200. The pedicle screw tulip 200 is configured to be attachable to, removable from, and re-attachable to the pedicle screw tower 100. The tower pedicle screw system 10 allows a user, such as a surgeon, to attach, remove, and reattach the pedicle screw tower 100 to the pedicle screw tulip 200 throughout the surgical procedure.

Figure 2A:
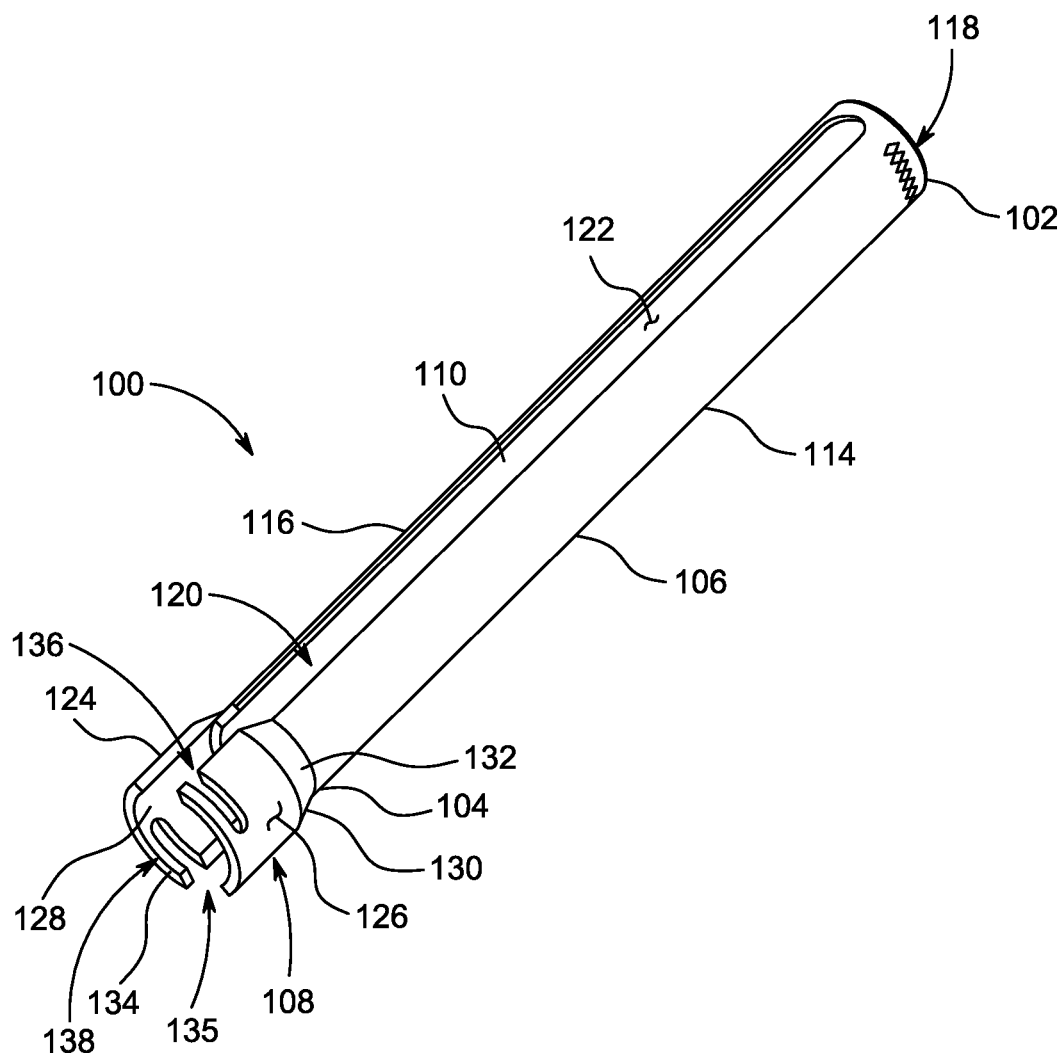
FIG. 2A is a perspective view of an illustrative embodiment of a pedicle screw tower associated with the tower pedicle screw system.
Figure 2B:
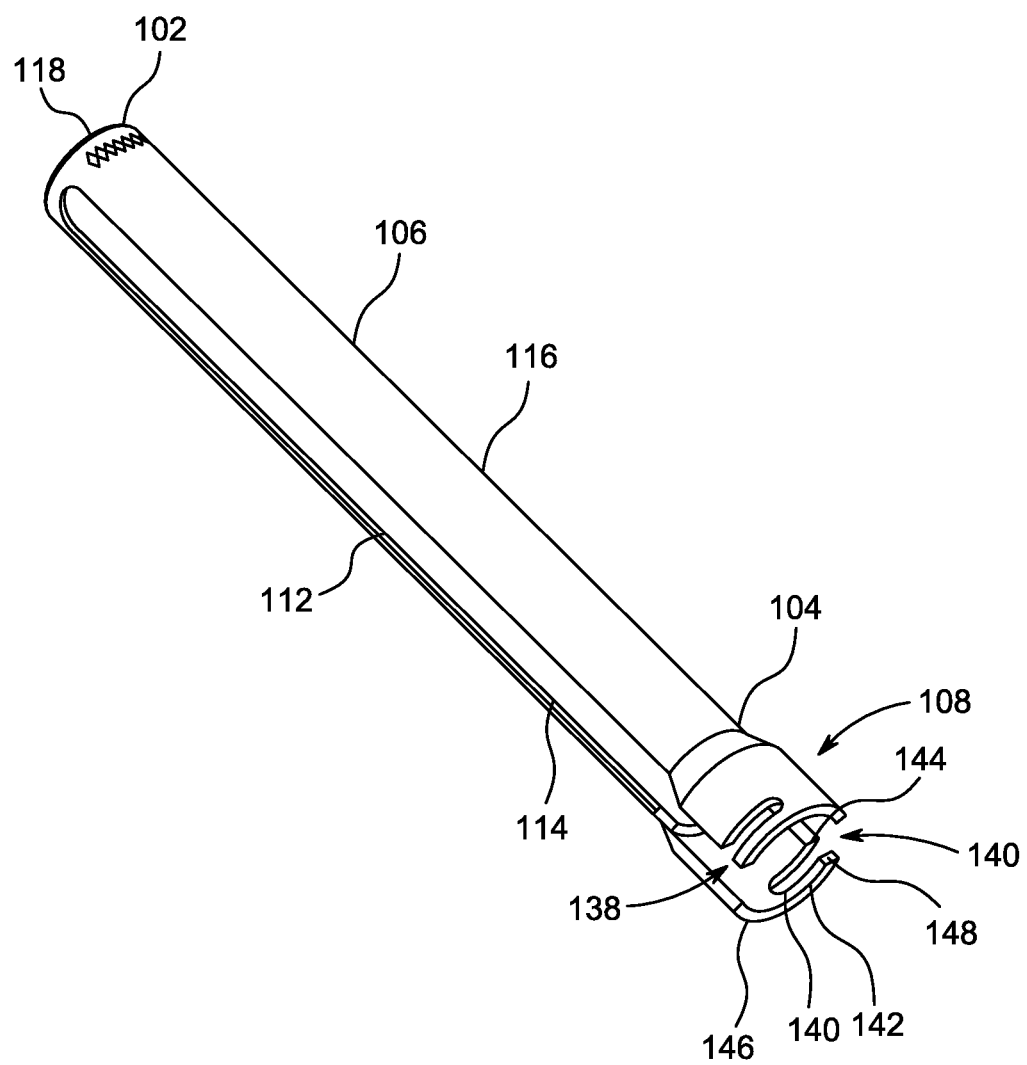
FIG. 2B is an alternative perspective view of the pedicle screw tower shown in FIG. 1A.

Referring to FIGS. 2A and 2B, the pedicle screw tower 100 comprises a first end 102, a second opposing end 104, and a main body 106 separating the first end 102 and the second opposing end 104. The main body 106 is shown as an elongated body, having a generally tube like shape. Secured to or integrally formed from the second end 104 is a pedicle screw engagement member 108. The pedicle screw engagement member 108 is configured to removably engage with at least two opposing portions or sections of the pedicle screw tulip 200. The pedicle screw tower 100 comprises a pair of longitudinal slotted openings or gap 110, 112 running from below the first end 102 and through the second end 102 and pedicle screw engagement member 108. The longitudinal slots or openings 110 and 112 divide the main body 106 into a right side portion 114 and a left side portion 116, thus providing for a left side pedicle screw engagement member 108 and a right side pedicle screw engagement member 108.

The first end 102 may terminate in an opening 118, allowing other medical devices or equipment, such as a spinal rod, to be inserted and move within an interior or inner lumen 120. The interior or inner lumen 120 is defined by an inner surface 122. By having the longitudinal slotted openings or gap 110, 112 extend below the first end 102, partial flexibility may be imparted on the right side portion 114 and the left side portion 116. In this case, the right side portion 114 or the left side portion 116 may be movable away from or towards the center of the main body 106 if a force is applied. The pedicle screw tower 100 may be made of a material that allows the right side portion 114 or the left side portion 116 to snap or move back to its original position once the force is removed. While illustrated with an opening 118, the pedicle screw tower 100 may also have a closed end. In addition, the main body 106 may not have longitudinal slotted openings or gap 110 and/or 112.

The pedicle screw engagement member 108 is configured to provide engagement with the pedicle screw tulip 200. The pedicle screw engagement member 108 is shown having a generally rounded main body 124 having an exterior surface 126 and an interior surface 128. The curvature of the interior surface 128 may be contoured to mirror the curvature of the portion of the pedicle screw tulip 200 it engages with. The pedicle screw engagement member main body 124 may have a diameter (inner or outer diameter) that is larger than the inner or outer diameter of the main body 106. The pedicle screw engagement member main body 124 may include a first end 130 secured to or integrally formed from the pedicle screw tower second end 104 via surface or wall 132. The surface or wall 132 is shown with a taper, but such orientation is not required. The pedicle screw engagement member main body 124 may include a second end 134, which terminates in an opening 135.

Figure 6:
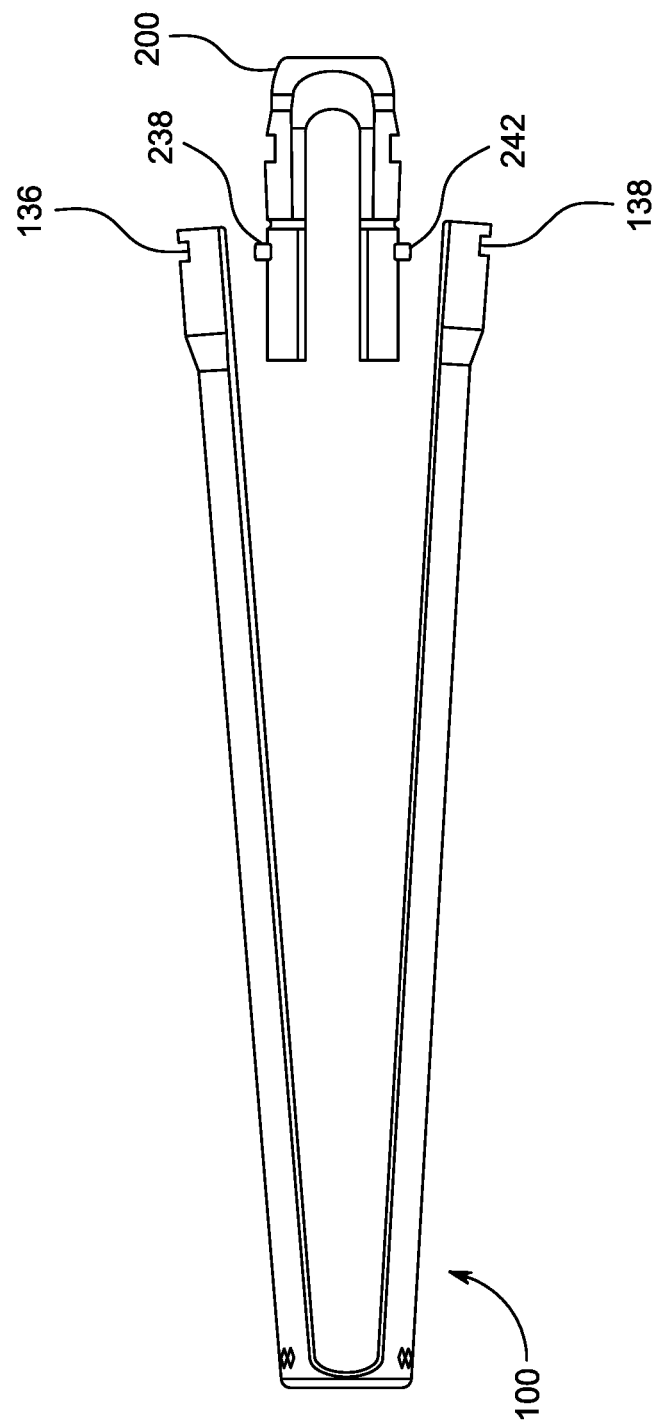
FIG. 6 is a side view of the pedicle screw tower, shown in an expanded position prior to engagement with the pedicle screw head.

The pedicle screw engagement member 108 preferably comprises two pedicle screw locking members 136 and 138, FIGS. 2A, 2B and 6, illustrated herein as a bayonet lock or opening 140. The first pedicle screw locking member 136 and the second pedicle screw locking member 138 are preferably arranged about 180 degrees opposite each other. The bayonet lock or opening 140 may be defined by a first side wall 142, a second opposing side wall 144, a terminal or closed end 146, and an open end 148. The distance between the first side wall 142 and the second opposing side wall 144 is sufficient to allow at least a portion of the pedicle screw tulip 200 to be positioned therebetween when the pedicle screw engagement member 108 moves, preferably in a linear direction left or right, thereabout, and/or allow at least a portion of the pedicle screw tulip 200 to rest within.

Figure 2C:
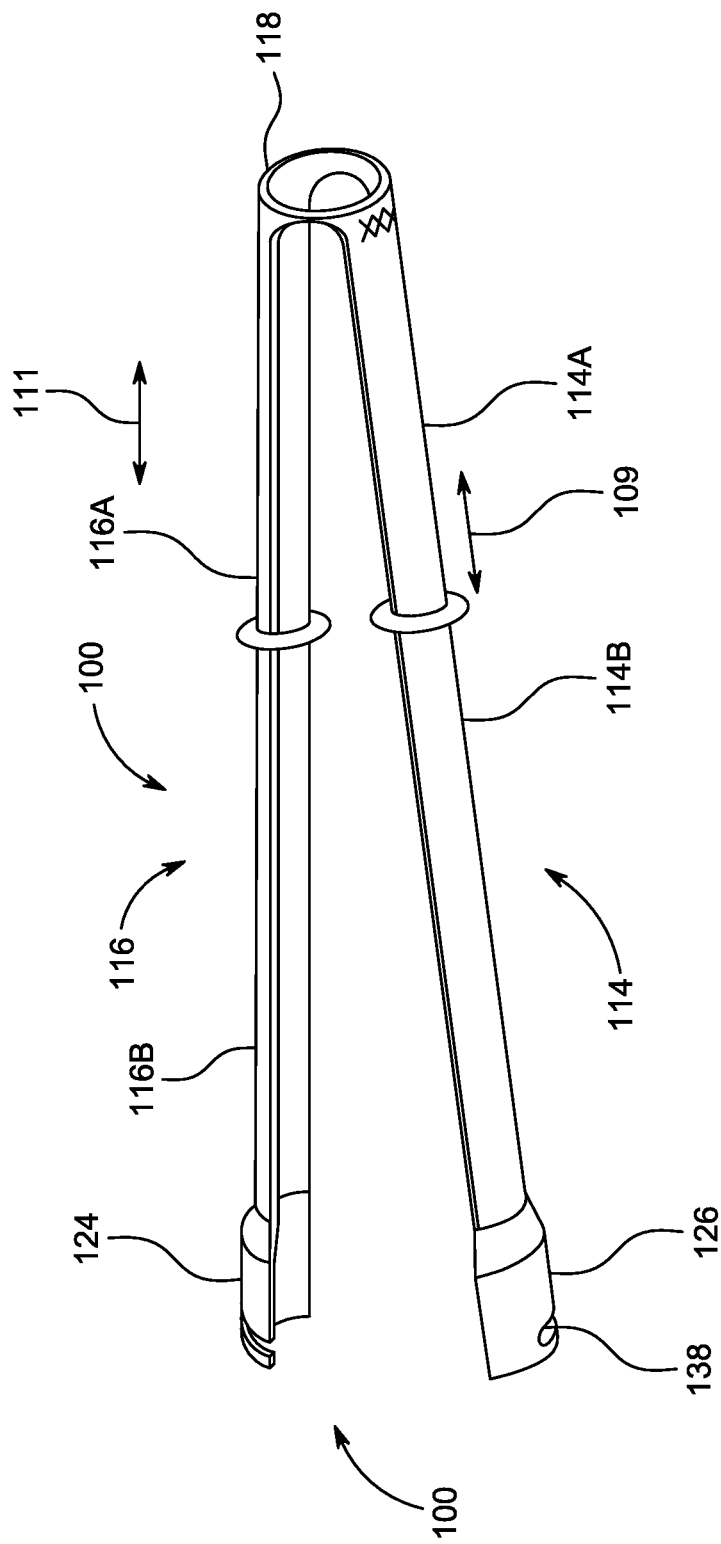
FIG. 2C illustrates an embodiment of the pedicle screw tower shown in FIG. 1A with height adjustment.

The pedicle screw tower 100 may be configured to be height adjustable to allow a user to keep at a level of an incision. Referring to FIG. 2C, the pedicle screw tower 100 is configured to be telescoping, so that the right side portion 114 comprises two independent portions, 114A and 114B. The right side portion 114A is configured to slide within 114B in a linear direction, see arrow 109. The left side portion 116 comprises two independent portions, 116A and 116B. The left side portion 116A is configured to slide within 116B in a linear direction, see arrow 111.

Figure 3A:
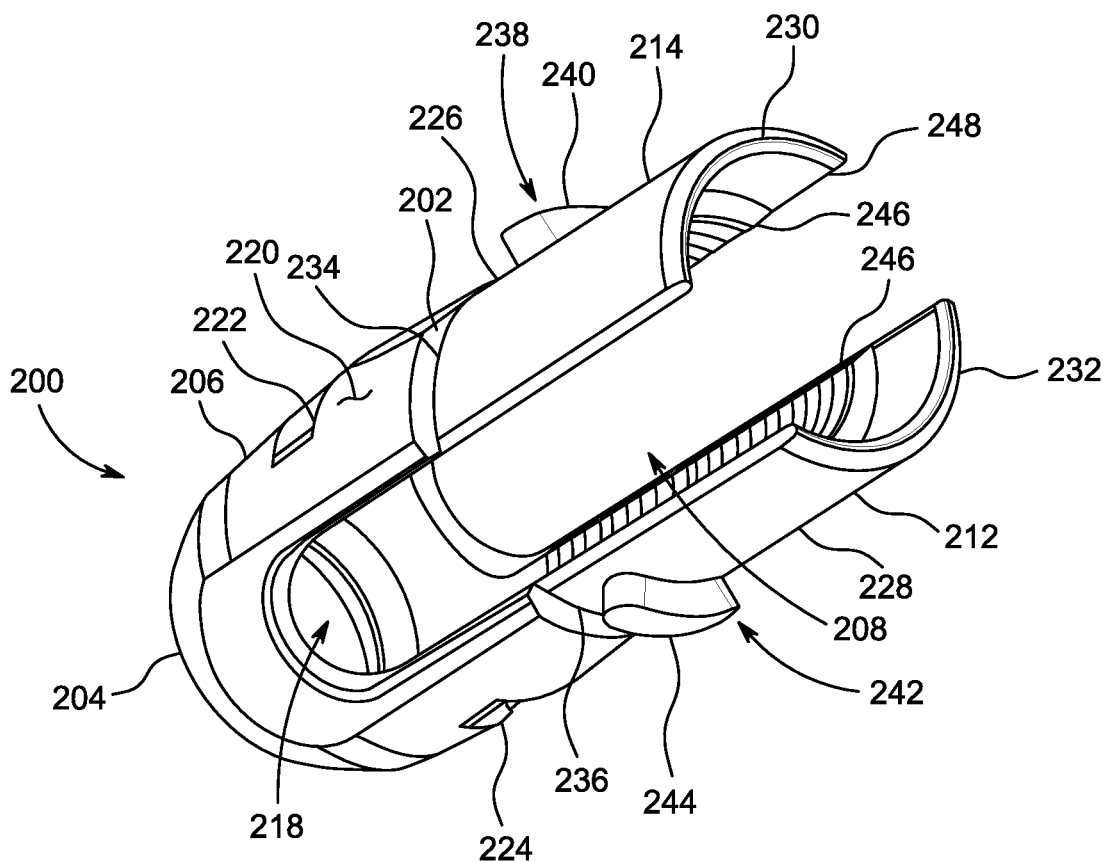
FIG. 3A is a perspective view of an illustrative embodiment of a pedicle screw head for use with the tower pedicle screw system.
Figure 3B:
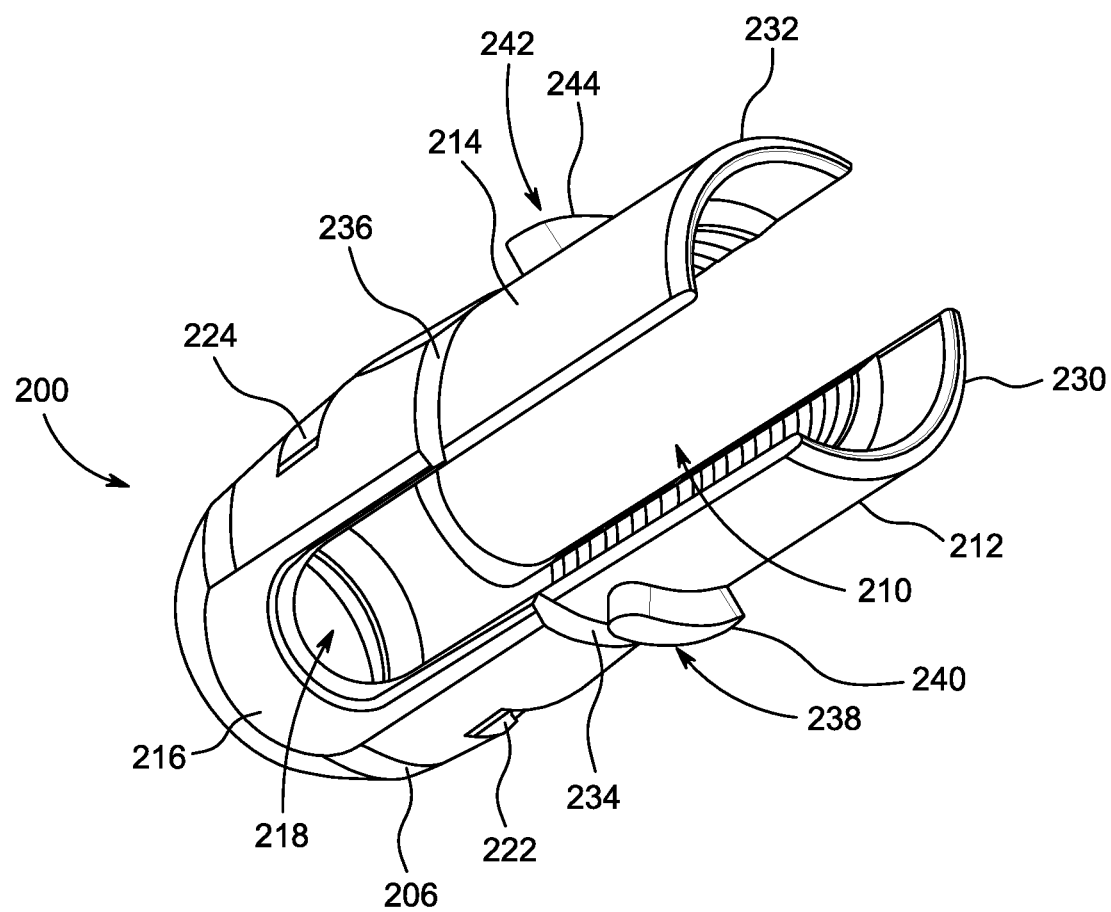
FIG. 3B is an alternative perspective view of the pedicle screw tower shown in FIG. 3A.

Referring to FIG. 3A and FIG. 3B, the pedicle screw tulip 200 comprises a first end 202, a second opposing end 204, and a main body 206 separating the first end 202 and the second opposing end 204. The pedicle screw tulip 200 comprises a pair of longitudinal slits or openings 208, 210 running from the first end 202 to the second opposing end 204. The longitudinal slits 208 and 210 divide the main body 206 into a left side portion 212 and a right side portion 214. The main body 206 is configured so the left side portion 212 and the right side portion 214 are connected at a base 216, assuming a U-shape. The second opposing end 204 comprises an opening 218 sized and shaped to receive and hold at least a portion of a pedicle screw body, such as a pedicle screw head (not shown). The outer surface 220 may have a conjugate shape or curvature as that of the interior surface 128 of the pedicle screw engagement member 108 so as to provide a proper fit when engaged therewith. The right side portion 214 may include a slotted channel 222. A secondary slotted channel 224, positioned on the left side portion 212 may be located around 180 degrees from the opening 222.

The left side portion 212 may include a left extension portion or wall 226, which extends from and upwardly, i.e. away from the second end 204. The right side portion 214 may include a right extension portion or wall 228, which extends from and upwardly, i.e. away from the second end 204. As illustrated, the longitudinal slotted openings or gaps 110 and 112 of the pedicle screw tower 100 continue upwardly and through the top surfaces or edges 230 and 232 of the left extension portion or wall 226 and the right extension portion or wall 228. Both the left side extension portion or wall 226 and the right side extension portion or wall 228 may connect to the left side portion 212 or right side portion 214 via a break line 234 and 236. Such break line allows a user to remove the left side extension portion or wall 226 and the right side extension portion or wall 228 from the left side portion 212 or the right side portion 214 via application of a sufficient force.

Positioned on the outer surface 220 of the pedicle screw tulip 200 is a first tower engagement member 238. The first tower engagement member 238 includes a body 240 located on the left side extension portion or wall 226 and is sized and shaped to allow the bayonet lock or opening 140 to move, preferably in a linear direction left or right, and engage with and/or rest or secure to the first pedicle screw locking member 136. A second tower engagement member 242 is located on the right side extension portion or wall 228 and is preferably positioned 180 degrees from the first tower engagement member 238. The second tower engagement member 242 includes a body 244 located on the right side extension portion or wall 228 and is sized and shaped to allow the bayonet lock or opening 140 to move, preferably in a linear direction left or right, and engage with and/or rest or secure to the second pedicle screw locking member 138.

The pedicle screw tulip 200 may include threading 246 on the internal surface 248). The threading 246 may extend the entire length of the pedicle screw tulip 200 or less than the entire length. The threading 246 may be located in the left side portion 212, the right side portion 214, the left side extension portion or wall 226, the right side extension portion or wall 228, or combinations thereof.

Figure 4:
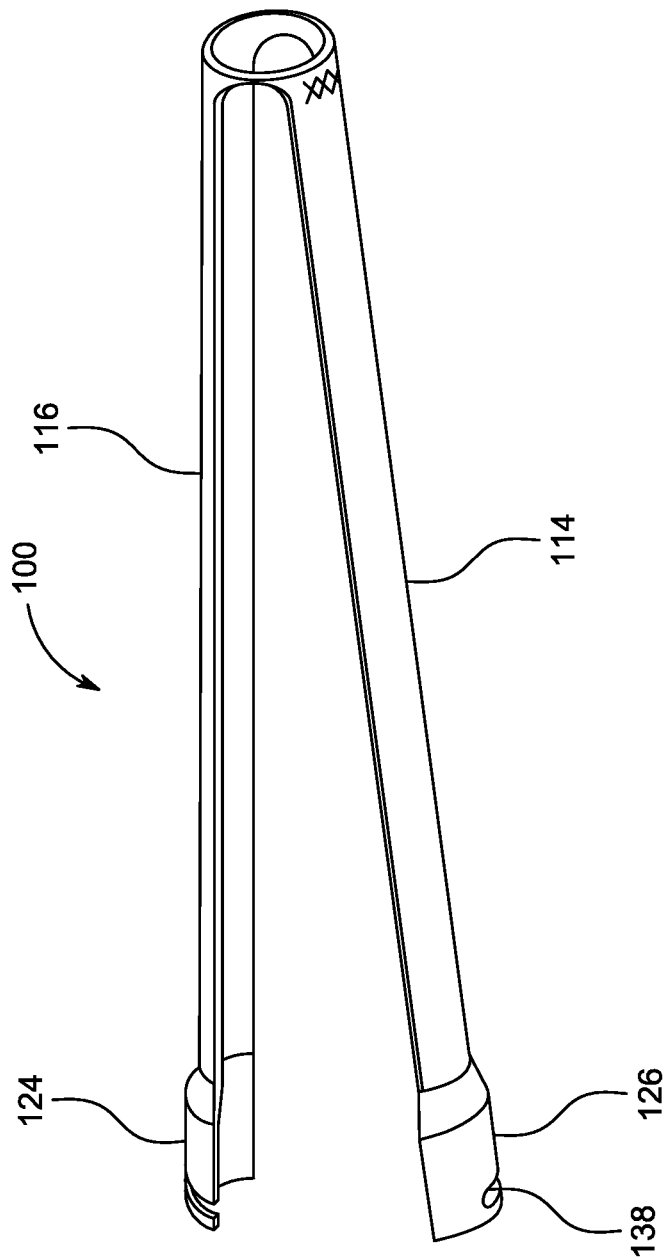
FIG. 4 is a side perspective view of the pedicle screw tower, shown in an expanded position prior to the pedicle screw head engaging position.
Figure 5:
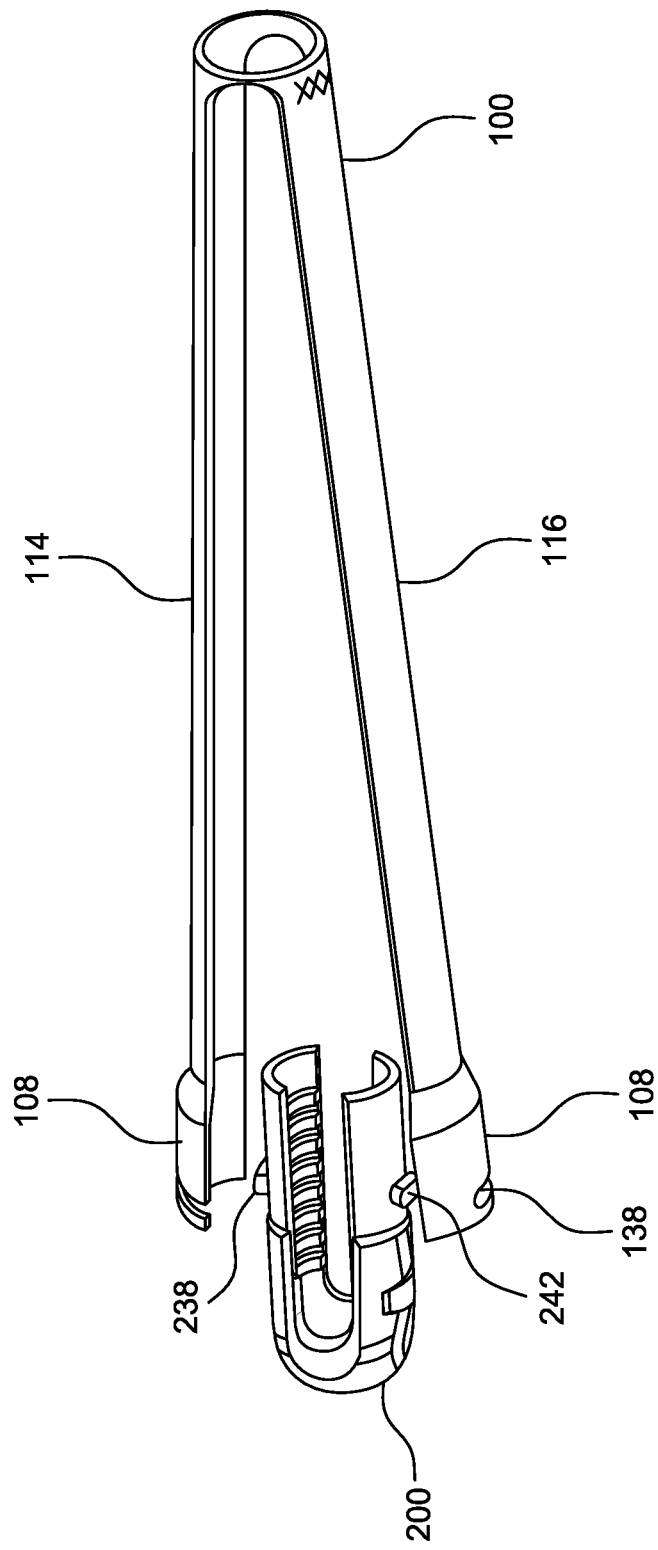
FIG. 5 illustrates the side perspective view of the pedicle screw tower, shown in an expanded position prior to engagement with the pedicle screw head.

Referring to FIG. 4, the pedicle screw tower 100 is shown in a pre-engagement position. In this pre-engagement position, the pedicle screw tower 100 is not engaging with any portion of the pedicle screw tulip 200. A user may then begin the engagement process, wherein the pedicle screw tower 100 and the pedicle screw tulip 200 align, engage, and secure to each other. FIGS. 5 and 6 illustrate the alignment process. In actual use, the surgeon would orientate the pedicle screw engagement member 108 of the pedicle screw tower 100 so the pedicle screw locking members 136 and 138 align with the first tower engagement member 238 and the second tower engagement member 242.

Figure 7:
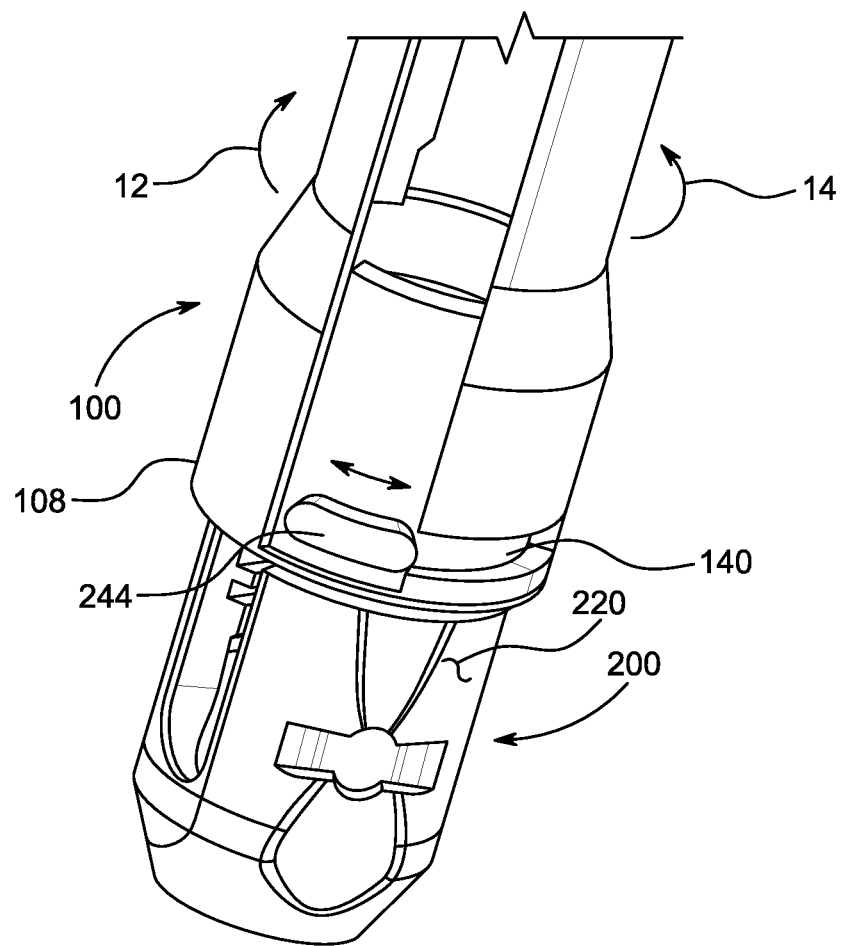
FIG. 7 illustrates the pedicle screw head being secured to the pedicle screw tower, shown with the tower placed in an unlocked position.
Figure 10:
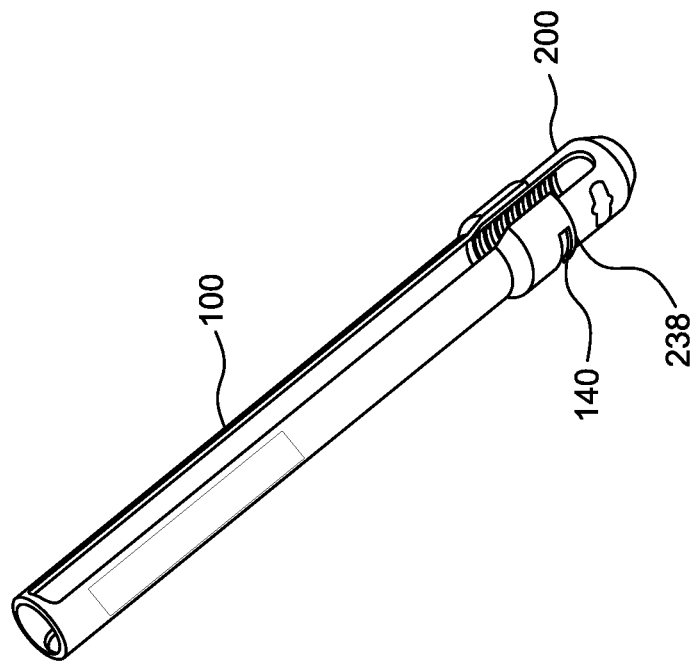
FIG. 10 is an alternative perspective view of the tower pedicle screw system, shown with the pedicle screw head engaged and secured to the pedicle screw tower.
Figure 9:
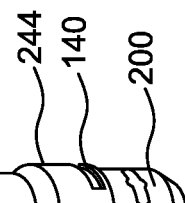
FIG. 9 is a perspective view of the tower pedicle screw system, shown with the pedicle screw head engaged and secured to the pedicle screw tower.
Figure 8:
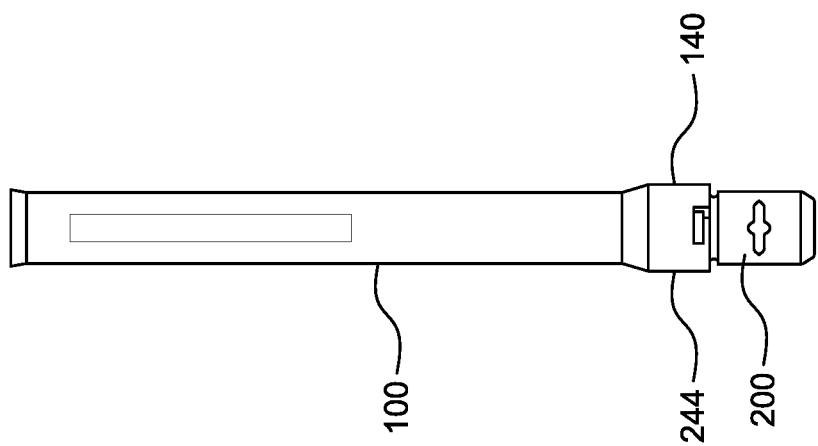
FIG. 8 is a front view of the tower pedicle screw system, shown with the pedicle screw head engaged and secured to the pedicle screw tower.
Figure 12B:
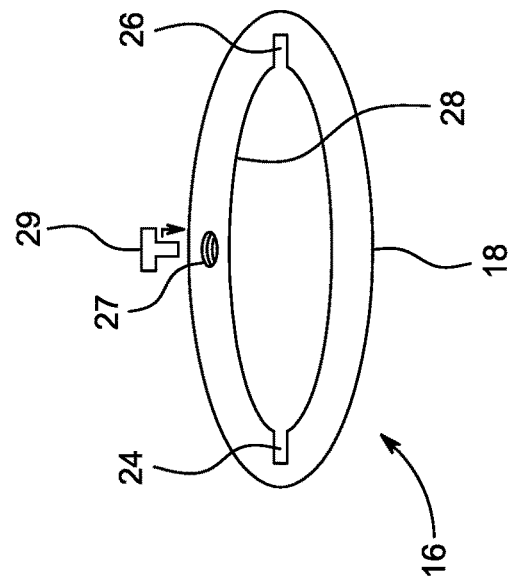
FIG. 12B is an alternative embodiment of the locking collar illustrated in FIG. 12A.
Figure 12A:
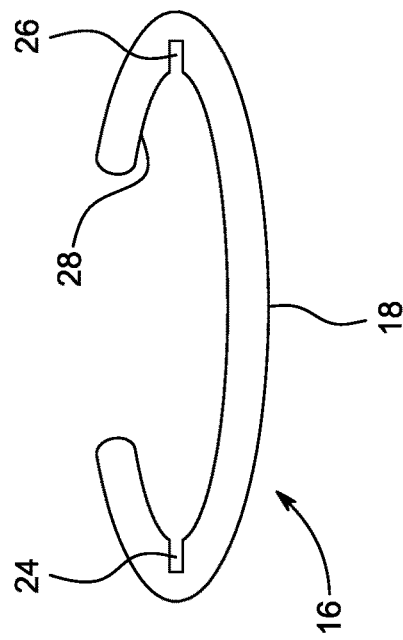
FIG. 12A is an alternative embodiment of a locking collar configured to lock the pedicle screw tower and the pedicle screw tulip.
Figure 11B:
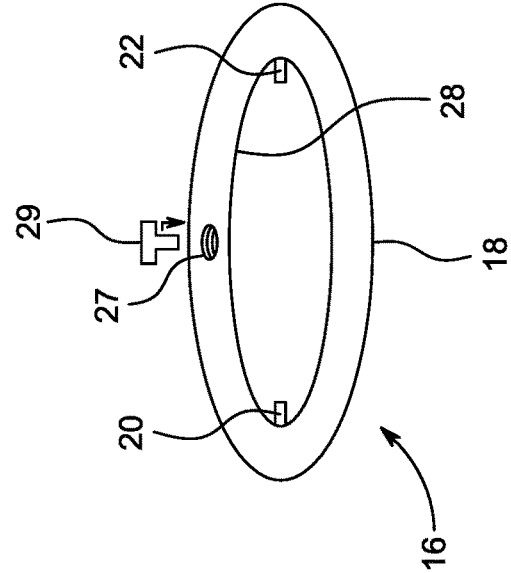
FIG. 11B is an alternative embodiment of the locking collar illustrated in FIG. 11A.
Figure 11A:
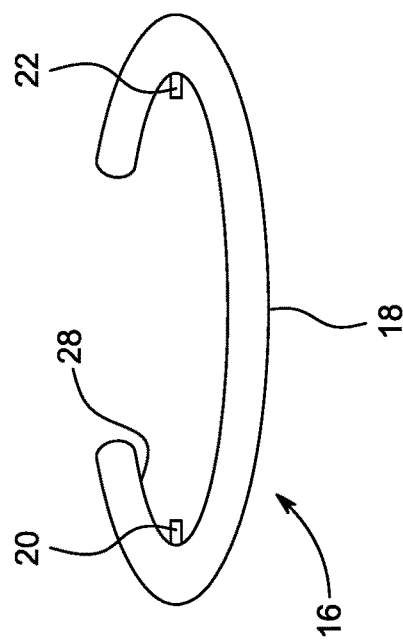
FIG. 11A is an illustrative embodiment of a tower-tulip locking component, illustrated as a locking collar configured to lock the pedicle screw tower and the pedicle screw tulip in position.

Referring to FIG. 7, the pedicle screw engagement member 108 is engaged with portions of the pedicle screw tulip 200. As shown, interior surface 128 (see FIG. 2A) of the pedicle screw engagement member main body contours (conjugate to) the shape and rests on top of the outer surface 220 of the left side extension portion or wall 226 and the right side extension portion or wall 228. As illustrated, the second tower engagement member body 244 is aligned with the bayonet lock or opening 140 of the pedicle first screw locking member 136. Although not illustrated, the first tower engagement member body 240 is aligned with the second bayonet lock or opening 140 of the pedicle second screw locking member 138. If the user turns the pedicle screw tower 100 in a clockwise orientation, see arrow 12, the bayonet lock or opening 140 moves to lock the second tower engagement member body 244 in place. At the same time, the second bayonet lock or opening 140 moves to lock the first tower engagement member body 138 in place. FIGS. 8-10 illustrate the pedicle screw tulip 200 being locked to the pedicle screw tower 100.

If the user turns the pedicle screw tower 100 in a counter-clockwise orientation, see arrow 14, bayonet lock or opening 140 moves to unlock the second tower engagement member body 244, i.e. the second tower engagement member body 244 is no longer positioned within the bayonet lock or opening 140. Such action of locking or unlocking allows the user the capability to attach, unattached, and reattach the pedicle screw tower 100 to the pedicle screw tulip 200.

The pedicle screw tower 100 and/or the pedicle screw tulip 200 may also be configured to prevent unintentional removal when secured together. As such, the tower pedicle screw system 10, the pedicle screw tower 100 and/or the pedicle screw tulip 200 may comprise a tower-tulip locking component configured to lock the pedicle screw tower 100 and/or the pedicle screw tulip 200, preventing the two from prematurely separating, particularly during a procedure. Referring to FIGS. 11A-12B, the tower pedicle screw system 10 may include a collar 16. The collar 16 may be made of a flexible material to aid in insertion or removal. The collar is preferably designed to be removable. The collar 16 may comprise a half ring (see FIGS. 11A and 12A) or ring-shaped body 18 (see FIGS. 11B and 12B) having one or more locking members, illustrated herein as two locking pins 20 and 22 or two inwardly recessed channels 24 and 26.

Both of the locking pins 20 and 22 or the inwardly recessed channels 24 and 26 are positioned on an inner surface 28 of the collar 16, and may be positioned on opposite sides of the inner surface 28, i.e. 180 degrees from each other. The locking pins 20 and 22 extend outwardly from the inner surface 28 and are positioned so that, when placed around the pedicle screw tower 100, the locking pins 20 and 22 are positioned within or near the opening of the screw locking members 136 and 138, thus closing off the bayonet lock or opening 140. The two inwardly recessed channels 24 and 26 extend into the inner surface 28 and are positioned so that, when placed around the pedicle screw tower 100, the inwardly recessed channels 24 and 26 align with the opening of the screw locking members 136 and 138, thus closing off the bayonet lock or opening 140.

While the half ring shaped body 18 (see FIGS. 11A and 12A) may allow the user to snap the collar 16 ON or OFF, other collar locking and removal mechanisms may be used. The ring shaped body 18 (see FIGS. 11B and 12B) may include collar locking receiving member 27, illustrated herein as a threaded opening. The threaded opening 27 is sized and shaped to receive, for example, a threaded screw 29 which could be screwed against a portion of the right side portion 114 or the left side portion 116 in a locked position.

Figure 13:
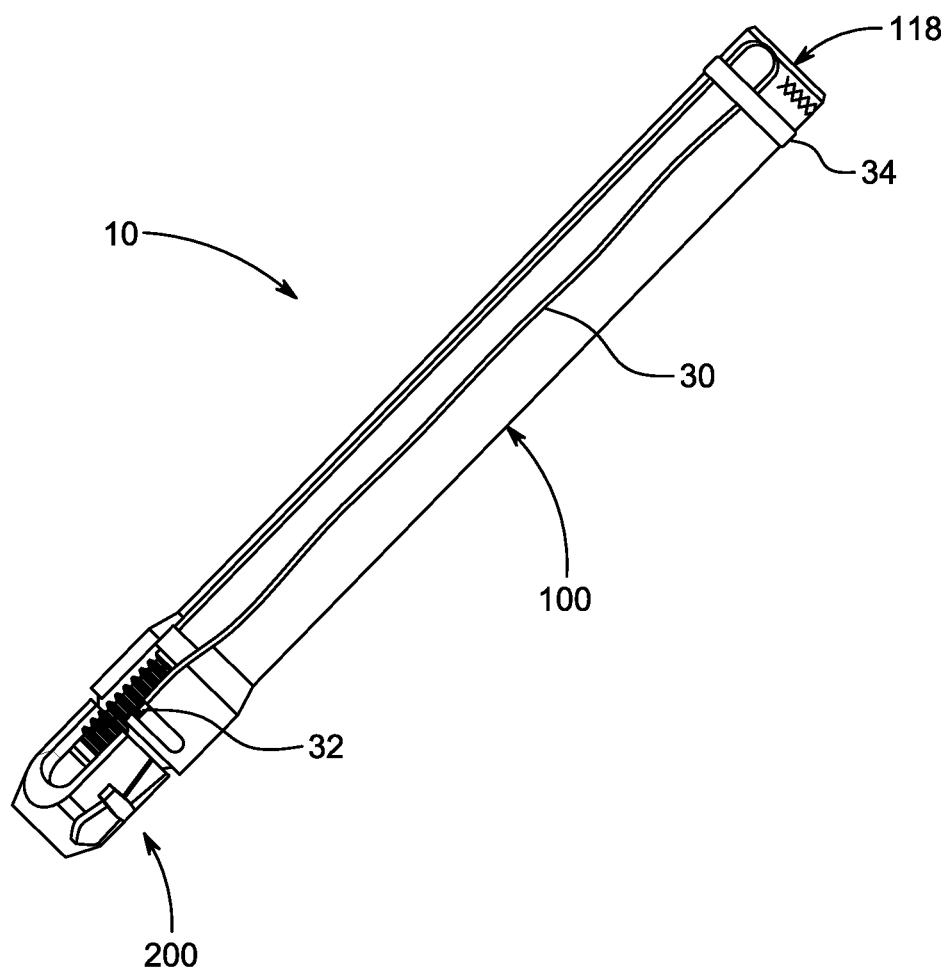
FIG. 13 illustrates another tower-tulip locking component.
Figure 14:
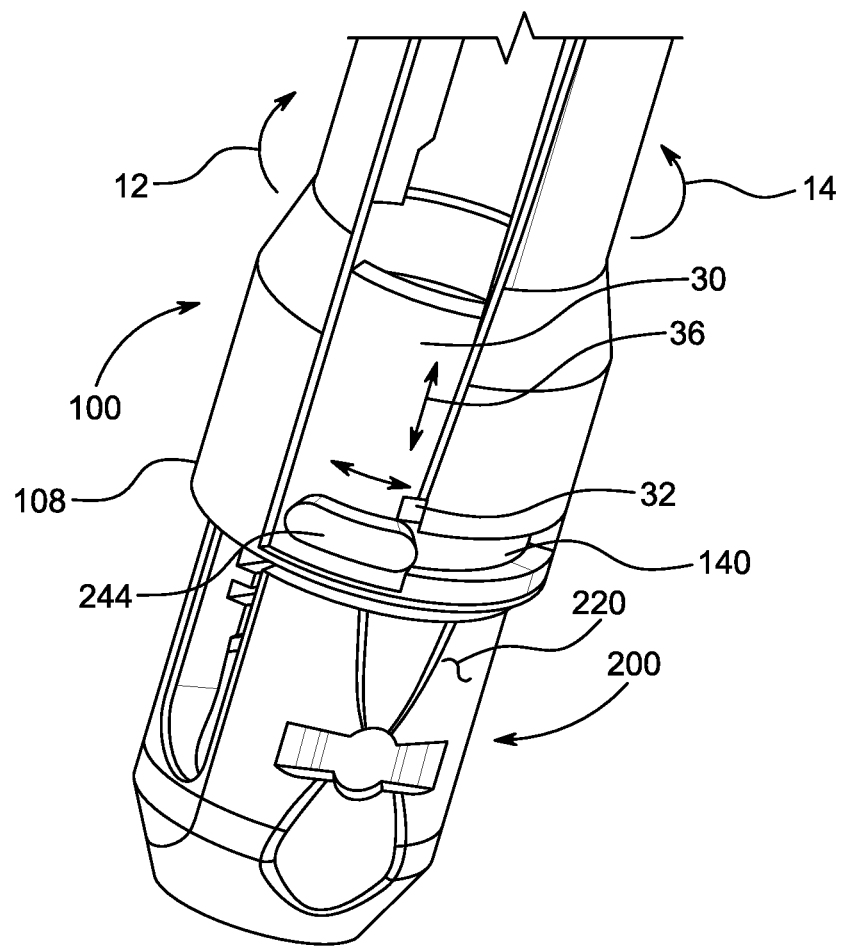
FIG. 14 is an alternative view of the tower-tulip locking component shown in FIG. 13.

Referring to FIGS. 13 and 14, an alternative tower-tulip locking component is illustrated. In this embodiment, the pedicle screw tower 100 uses a locking system comprising an elongated member, illustrated as a wire 30 running along the length of the pedicle screw tower 100. While described as using wire, other flexible thread, strand, or rod, metal or other materials, may be used. At one end of the wire 30 is the locking pin 32. The locking pin 32 is configured to be positioned to align with or be inserted into the opening of the screw locking members 136 and 138, thus closing off the bayonet lock or opening 140 in the locked position. When not in the locked position, the locking pin 32 may be positioned just above or below (see FIG. 14) the screw locking member 136 and/or 138. At the other end, the wire 30 may be operatively coupled to an actuating device 34, such as a knob, that when rotated, moves the locking pin 32 in a linear direction, see arrow 36. Although not illustrated, the wire 30 may be placed within a channel to maintain it in a fixed location.

Figure 15:
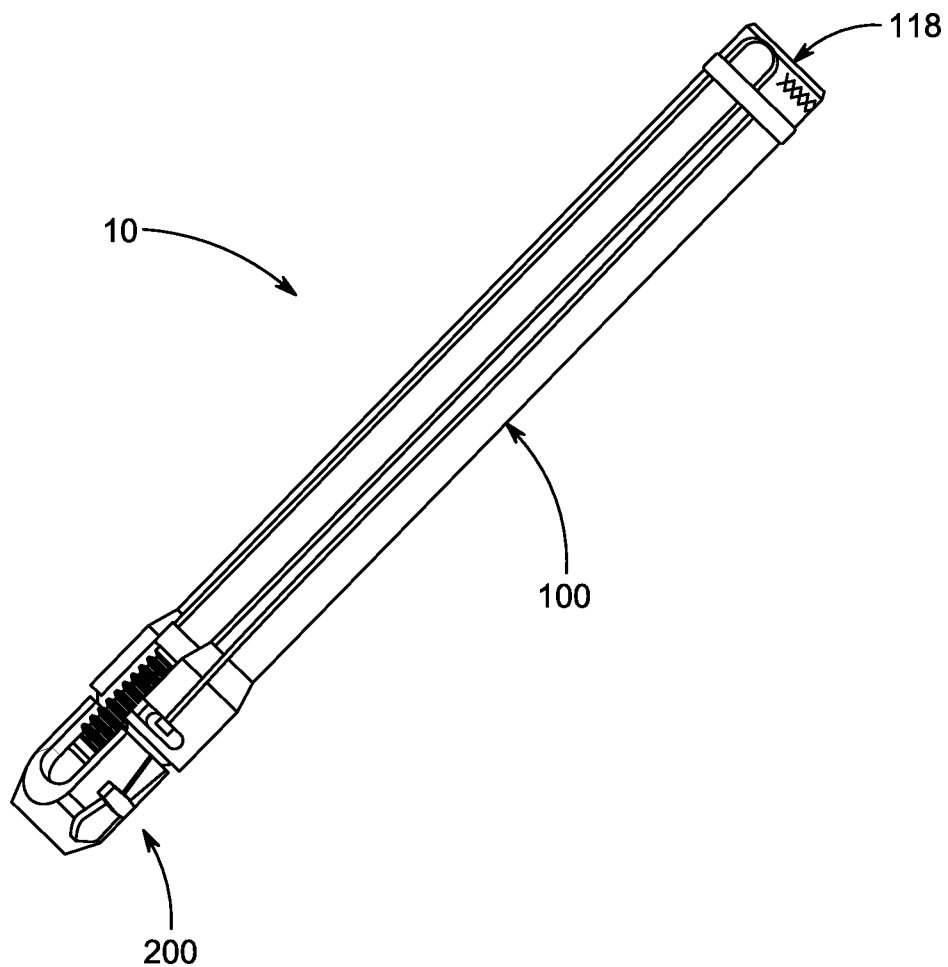
FIG. 15 illustrates an additional tower-tulip locking component.
Figure 16:
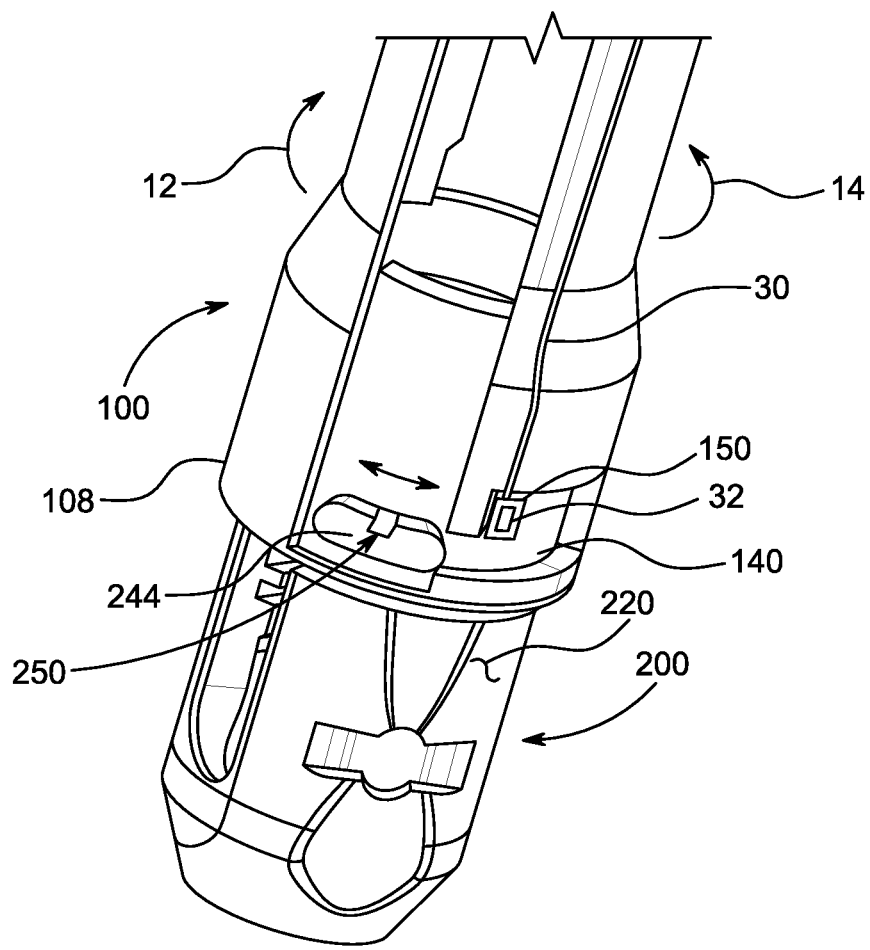
FIG. 16 is an alternative view of the tower-tulip locking component shown in FIG. 15.

Referring to FIGS. 15 and 16, an alternative tower-tulip locking component is illustrated. The locking system utilizes the same wire 30, locking pin 32, and actuating device 34. In this embodiment, locking pin 32 is positioned within a tower locking pin receiving member 150, illustrated herein as a cut out section located along the pedicle screw locking member 136 and/or 138. The locking pin 32 is sized and shaped to fit within and secure to a tulip locking pin receiving member 250, illustrated herein as a cut out section positioned within the first or second tower engagement member bodies 240 or 244. When the first or second tower engagement member bodies 240 or 244 are positioned within the screw locking member 136 and/or 138, the tower locking pin receiving member 150 and the tulip locking pin receiving member 250 are aligned or stacked. In the locked position (see FIG. 15), the locking pin 32 engages with and rests within the tulip locking pin receiving member 250. In the unlocked position (see FIG. 16), the locking pin 32 rests within the tower locking pin receiving member 150.

Figure 17:
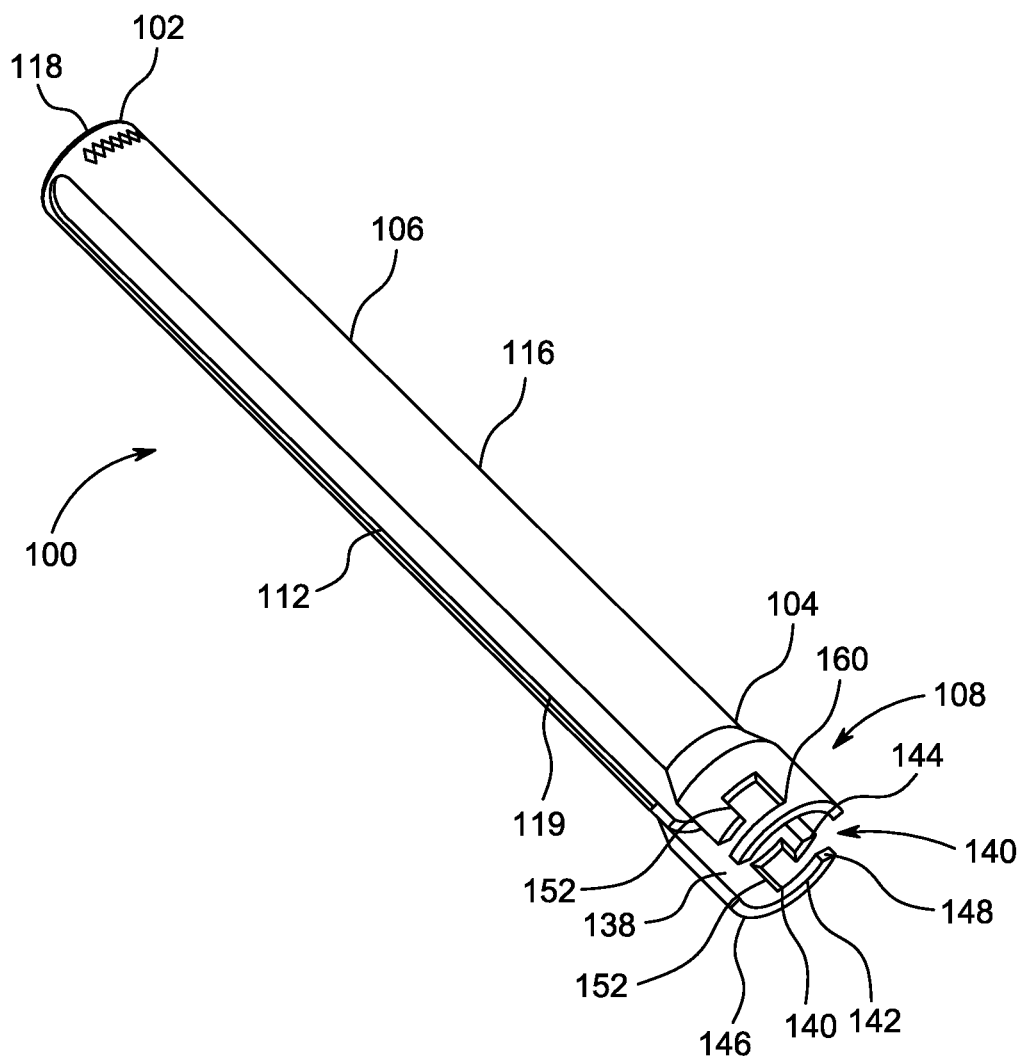
FIG. 17 illustrates an embodiment of the pedicle screw tower with a tower engagement receiving member.
Figure 18:
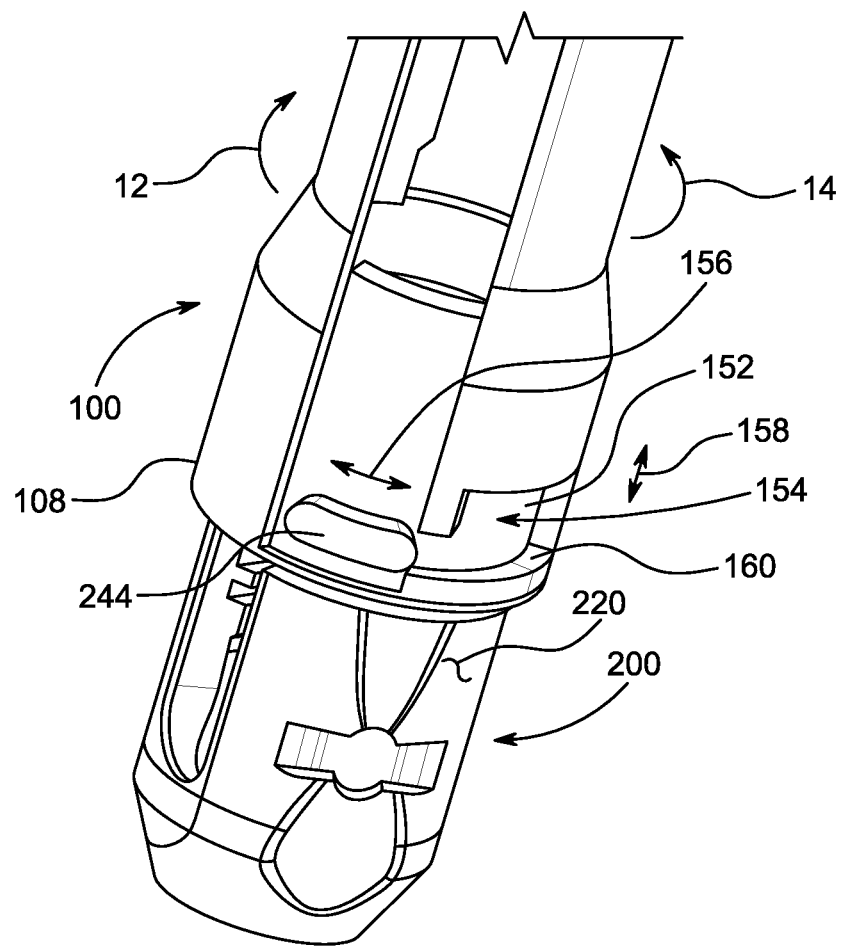
FIG. 18 illustrates the pedicle screw tower with the tower engagement receiving member shown in FIG. 17, with the pedicle screw tulip.
Figure 19:
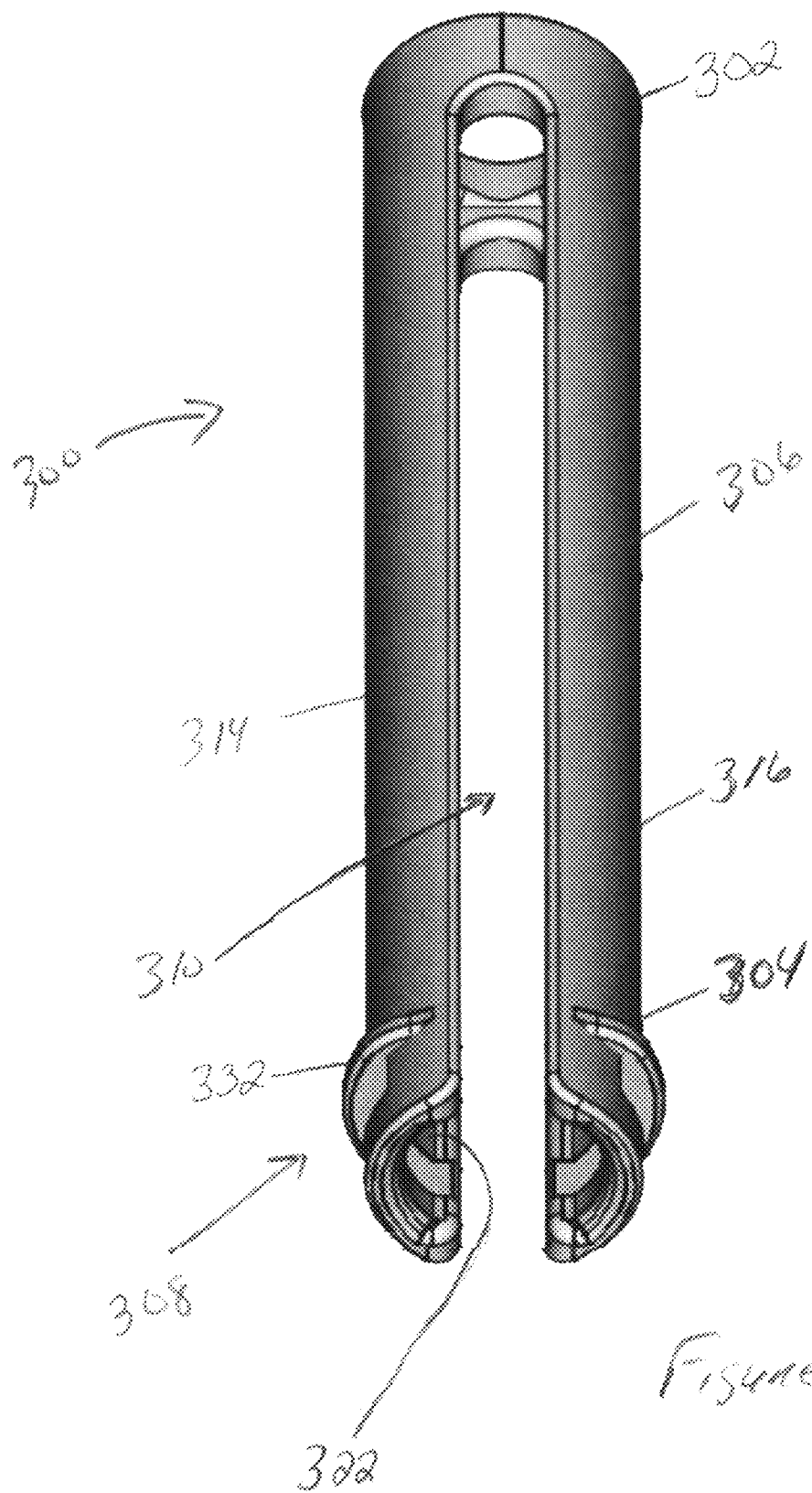
FIG. 19 illustrates a perspective view of an embodiment of the pedicle screw tower with snap fit pedicle screw locking members.
Figure 20:
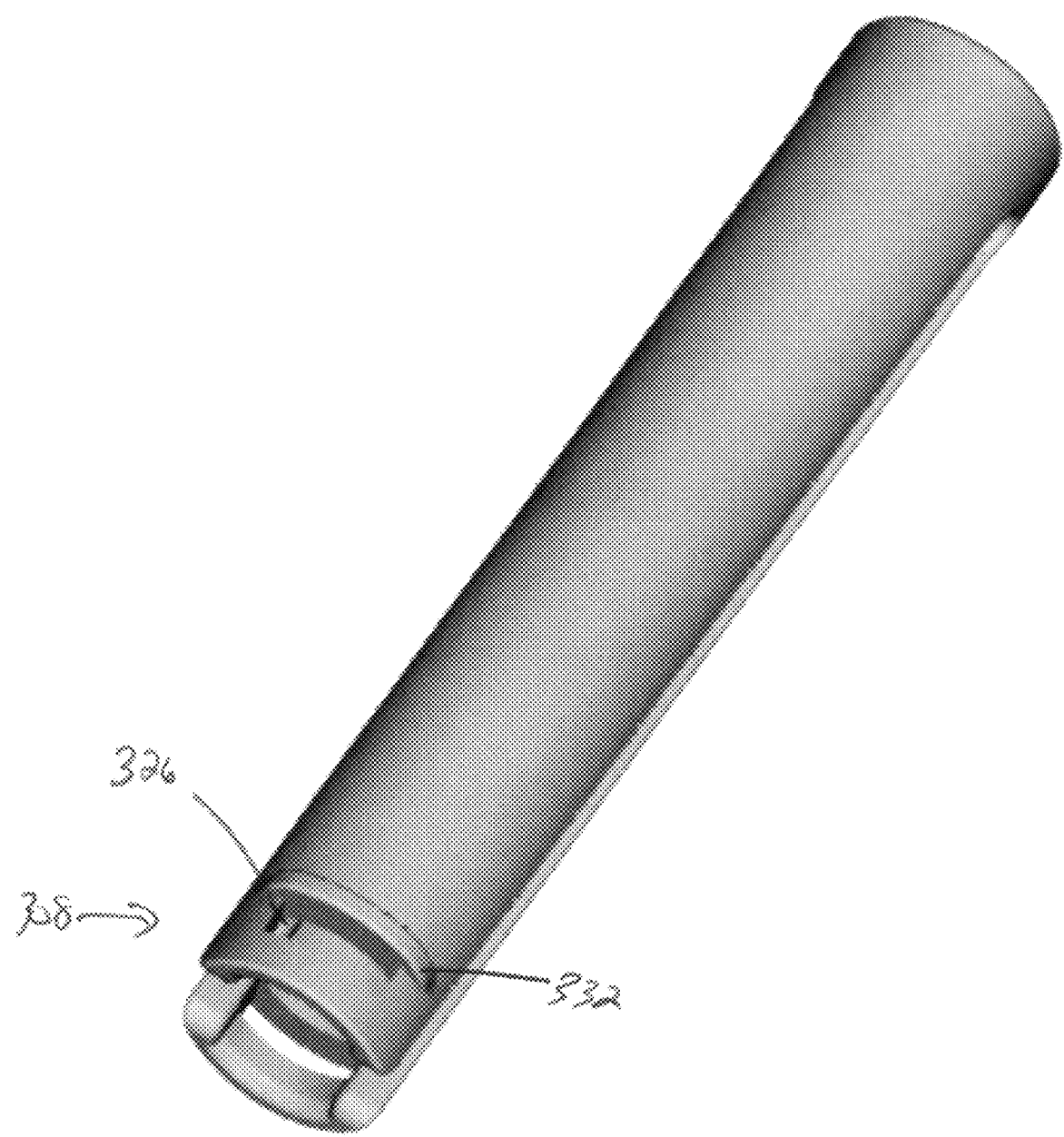
FIG. 20 is a bottom perspective view of the pedicle screw tower with snap fit pedicle screw locking members, as illustrated in FIG. 19.
Figure 21:
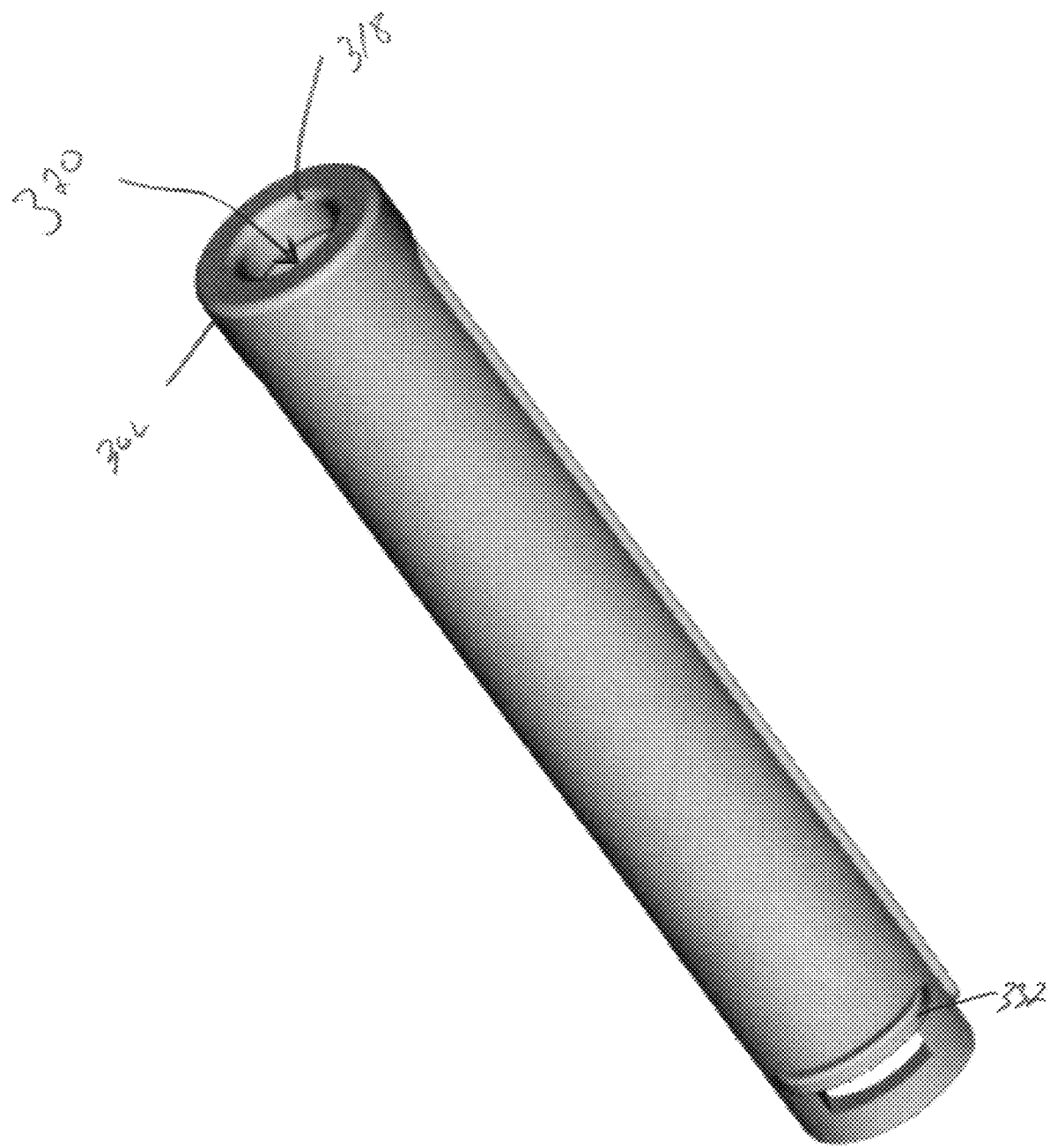
FIG. 21 is a top perspective view of the pedicle screw tower with snap fit pedicle screw locking members, as illustrated in FIG. 19.
Figure 22A:
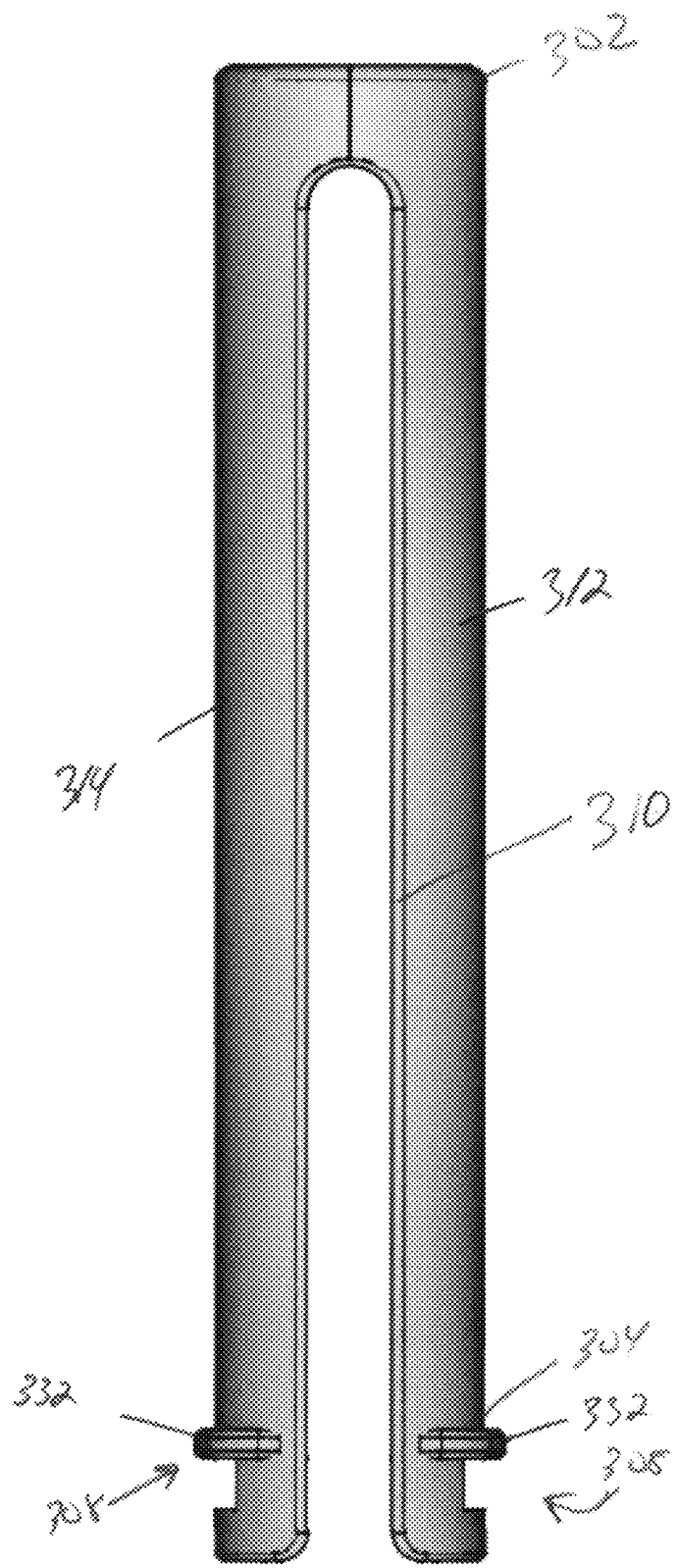
FIG. 22A is a side view of the pedicle screw tower with snap fit pedicle screw locking members, as illustrated in FIG. 19.
Figure 22B:
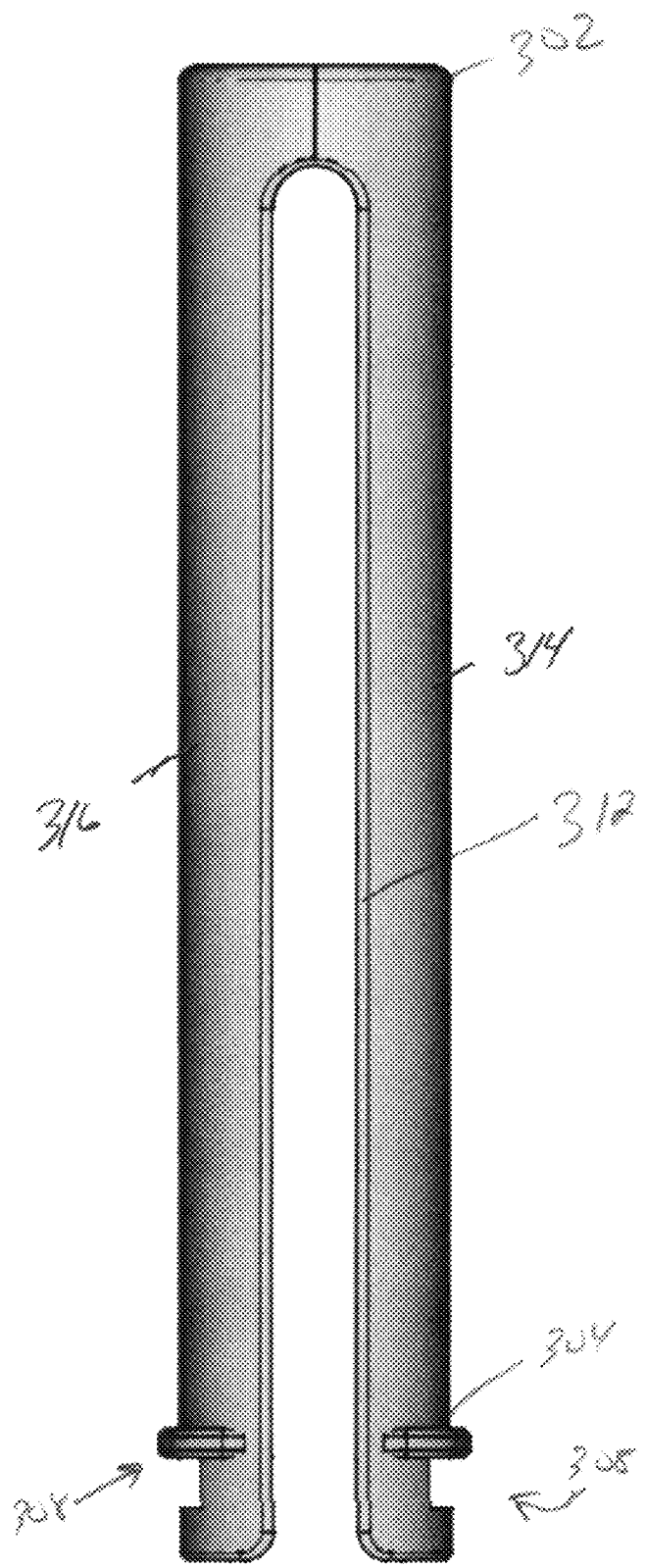
FIG. 22B is an alternative side view of the pedicle screw tower with snap fit pedicle screw locking members, as illustrated in FIG. 19.

Referring to FIGS. 17 and 18, the pedicle screw tower 100 is shown with a tower engagement receiving member(s) 152, illustrated herein as opening(s) 154 formed from a cut out section(s) within the pedicle screw tower 100. The tower engagement receiving member 152 is positioned at the corner of the bayonet lock or opening 140 of the first pedicle screw locking member 136 and/or the second pedicle screw locking member 138, with the opening 154 extending horizontally towards the bayonet lock or opening 140 and upward, or vertically along a pedicle screw tower 100 vertical longitudinal axis. Whereas the bayonet lock or opening 140 is placed in positon or accessed by movement in the linear direction, left to right/right to left, see arrow 156 (FIG. 18), and the tower engagement receiving member 152 is placed in position or accessed in a linear direction, down to up/up to down, see arrow 158. In this embodiment, the locking pin 32 is not required.

To lock in place, the user rotates the pedicle screw tower 100 so the first tower engagement member body 240 or the second tower engagement member body 244 slides into the bayonet lock or opening 140 of the first pedicle screw locking member 136 or the second pedicle screw locking member 138, resting or stopping at the corner 160. Once at this position, the user can push the pedicle screw tower 100 down to place and lock the first tower engagement member body 240 or the second tower engagement member body 244 within the tower locking pin receiving member 152. The size and shape of the tower engagement receiving member 152 is sufficient to receive and maintain the first tower engagement member body 240 or the second tower engagement member body 244 therein until a second force is applied to the pedicle screw tower 100, removing them out.

Referring to FIGS. 19-22, an illustrative example the tower pedicle screw system with a snap fit pedicle screw locking member, referred to as tower pedicle screw system 300 is shown. The tower pedicle screw system 300 may include many of the same structural components and many of the same functions as described previously. The pedicle screw tower 300 comprises a first end 302, a second opposing end 304, and a main body 306 separating the first end 302 and the second opposing end 304. The main body 306 is shown as an elongated body, having a generally tube like shape. Secured to or integrally formed from the second end 304 is a pedicle screw engagement member 308. The pedicle screw engagement member 308 is configured to removably engage with a portion or section of a conjugate or keyed pedicle screw tulip 324 (see FIGS. 24A-24C). The pedicle screw tower 300 comprises a pair of longitudinal slotted openings or gaps 310, 312 running from below the first end 302 and through the second end 304 and pedicle screw engagement member 308. The longitudinal slotted openings or gaps 310 and 312 divide the main body 306 into a right side portion 314 and a left side portion 316. The right side portion 314 includes a pedicle screw engagement member 308. The left side portion 316 includes a pedicle screw engagement member 308.

The first end 302 may terminate in an opening 318, allowing other medical devices or equipment to be inserted and move within an interior or inner lumen 320. The interior or inner lumen 320 is defined by an inner surface 322. By having the longitudinal slits or openings 310, 312 extend below the first end 302, partial flexibility may be imparted on the right side portion 314 and the left side portion 316. In this case, the right side portion 314 or the left side portion 316 may be movable, away from or towards the center of the main body 306 if a force is applied. The pedicle screw tower 300 may be made of a material that allows the right side portion 314 or the left side portion 316 to snap or move back to its original position once the force is removed. While illustrated with an opening 318, the pedicle screw tower 300 may also have a closed end. In addition, the main body 306 may not have longitudinal slotted openings or gaps 310 and/or 312.

The pedicle screw engagement members 308 are configured to provide engagement with the pedicle screw tulip 324. The pedicle screw engagement members 308 is shown having a pedicle screw tulip receiving portion 326, illustrated herein as a slotted opening. The pedicle screw tulip receiving portion 326 is sized and shaped to receive and hold therein at least a portion of the pedicle screw tulip 324. The pedicle screw engagement members 308 may also include a pedicle screw tulip engagement area 328, see FIG. 23. The pedicle screw tulip engagement area 328 may be defined by the area below the pedicle screw tulip receiving portion 326 to the distal or bottom surface 330 of the tower pedicle screw system 300. The pedicle screw tulip engagement area 328 is sized and shaped to engage with and fit within a portion of the pedicle screw tulip 324. Toward the proximal end (toward the first end 102) of the pedicle screw tulip receiving portion 326, the pedicle screw engagement members 308 may include shelf 332, formed as a flanged body or protuberance 332. The shelf 332 acts as a stop for the tower locker-rod pusher or sleeve 360, preventing over-threading. Once the tower locker-rod pusher or sleeve 360 hits the shelf 332, a user knows it is locked in.

Figure 24A:
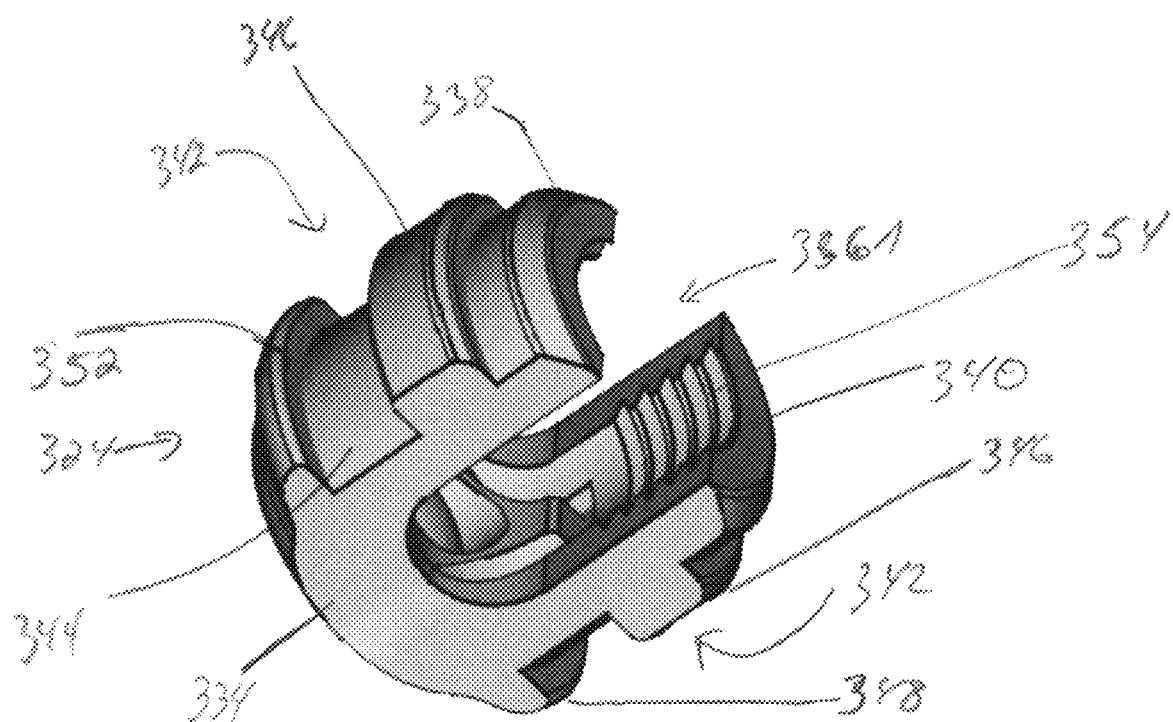
FIG. 24A is a perspective view of an illustrative embodiment of a pedicle screw tulip head keyed to fit within the pedicle screw tower with the snap fit pedicle screw locking members illustrated in FIG. 19.
Figure 24B:
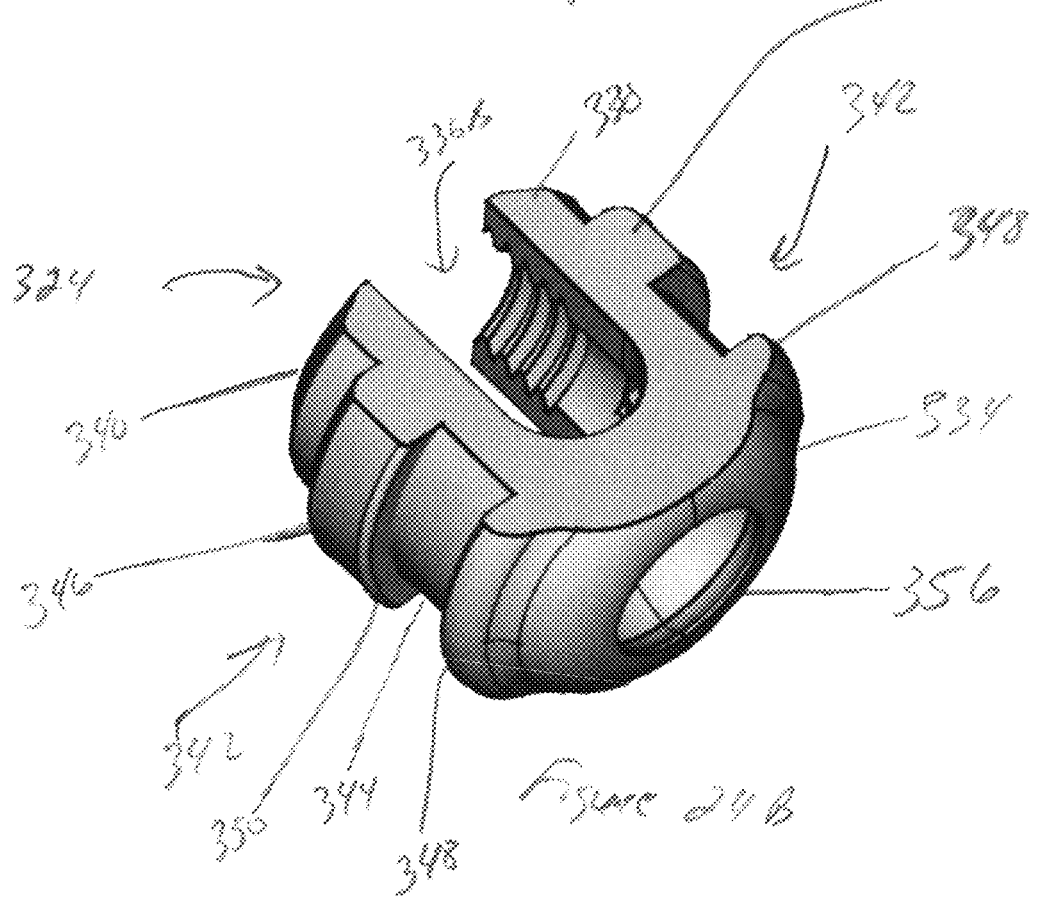
FIG. 24B is an alternative perspective view of the pedicle screw tulip head shown in FIG. 24A.
Figure 24C:
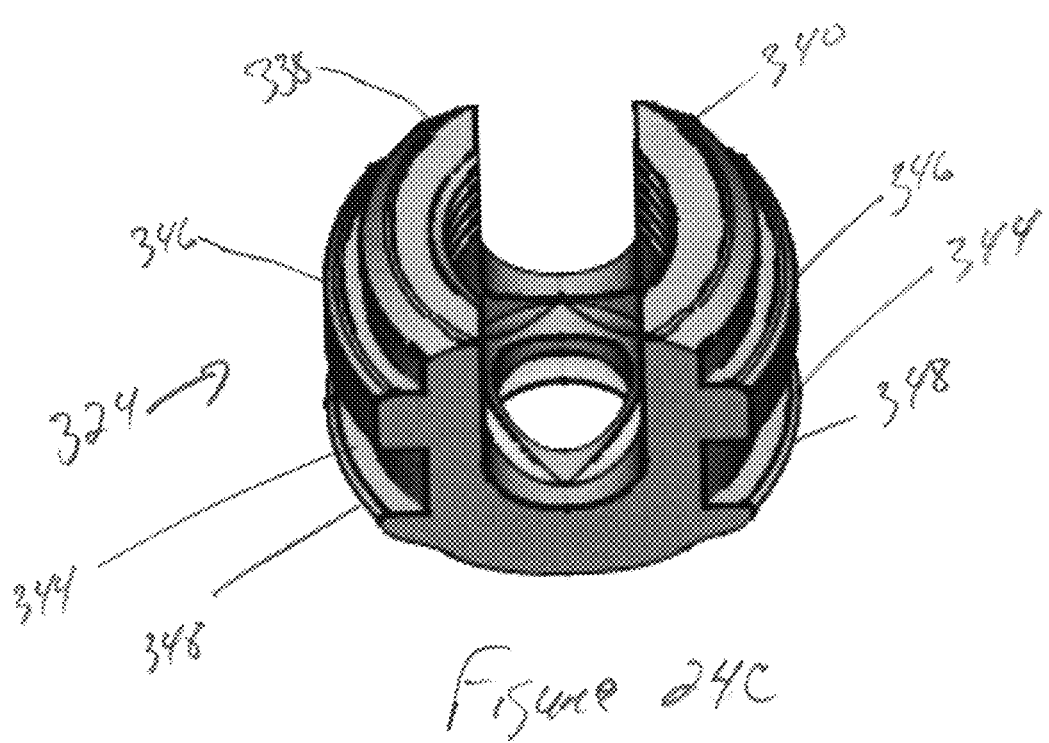
FIG. 24C is an alternative view of the pedicle screw tulip head shown in FIG. 24A.
Figure 25:
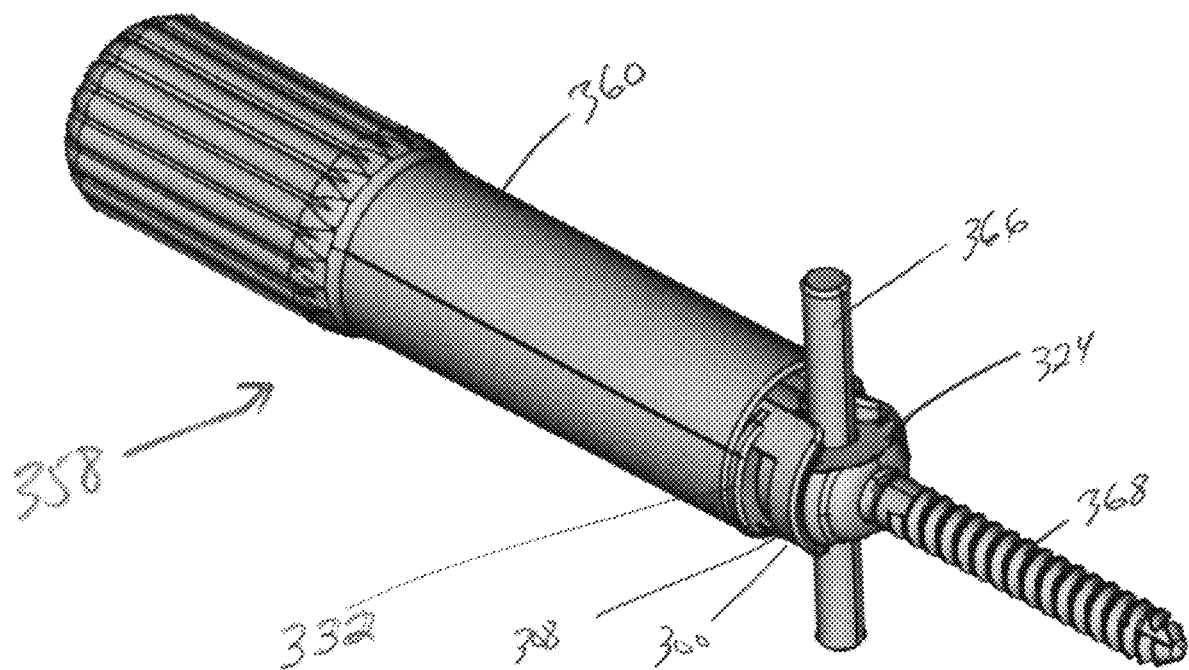
FIG. 25 is a perspective view of an illustrative embodiment of a snap fit tower assembly.
Figure 2C:
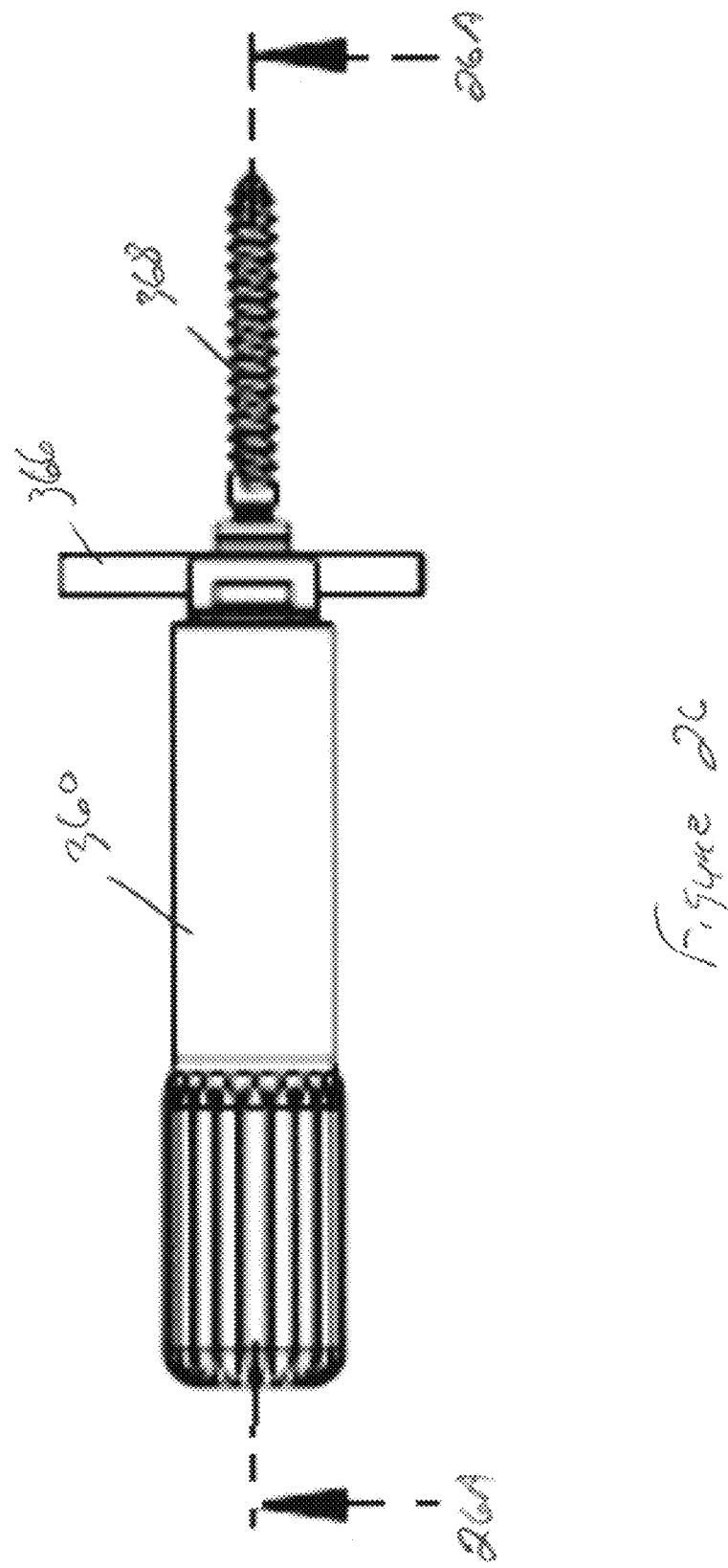
Figure 27:
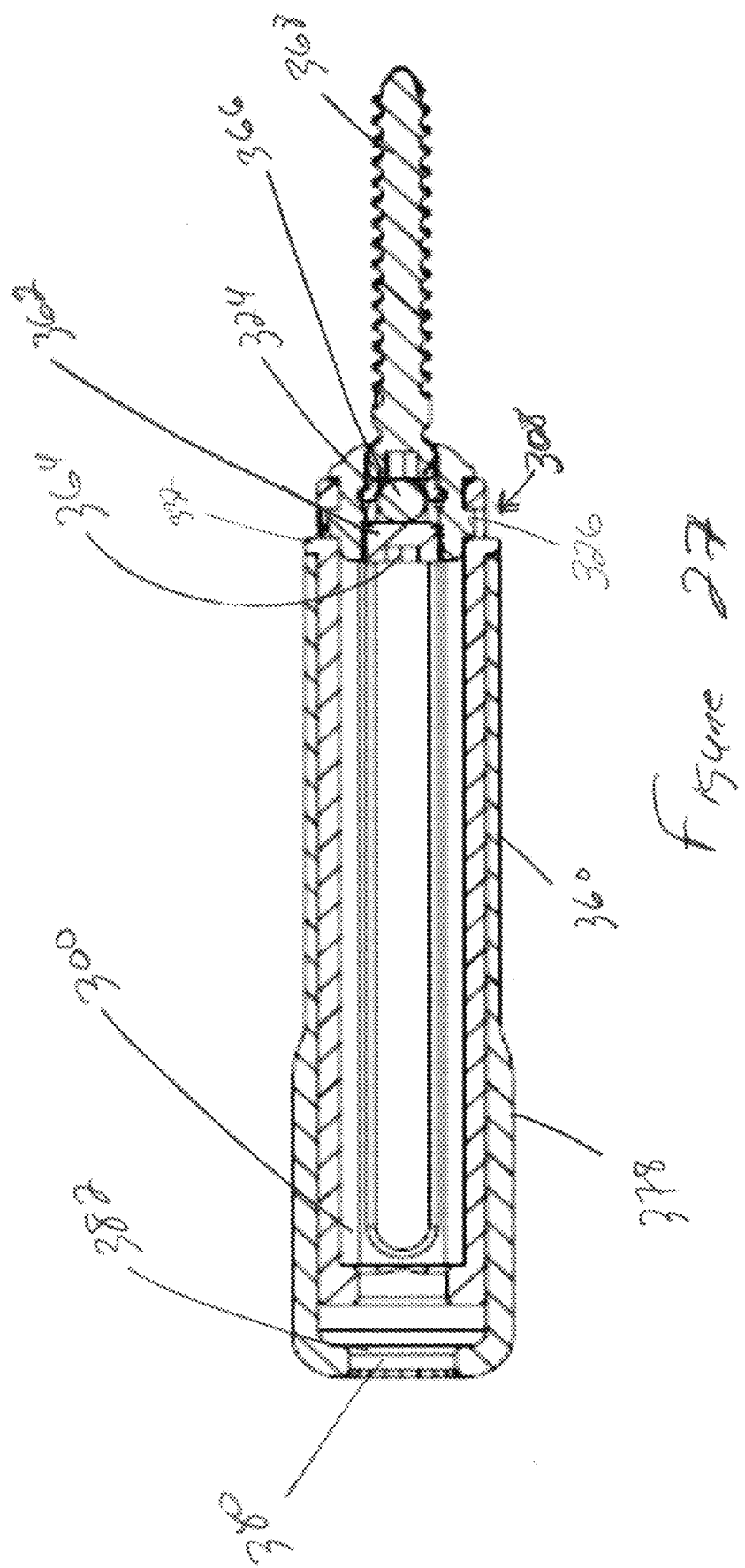
FIG. 27 is a cross-sectional view of the snap fit tower assembly taken along lines 26A-26A of FIG. 26.
Figure 28:
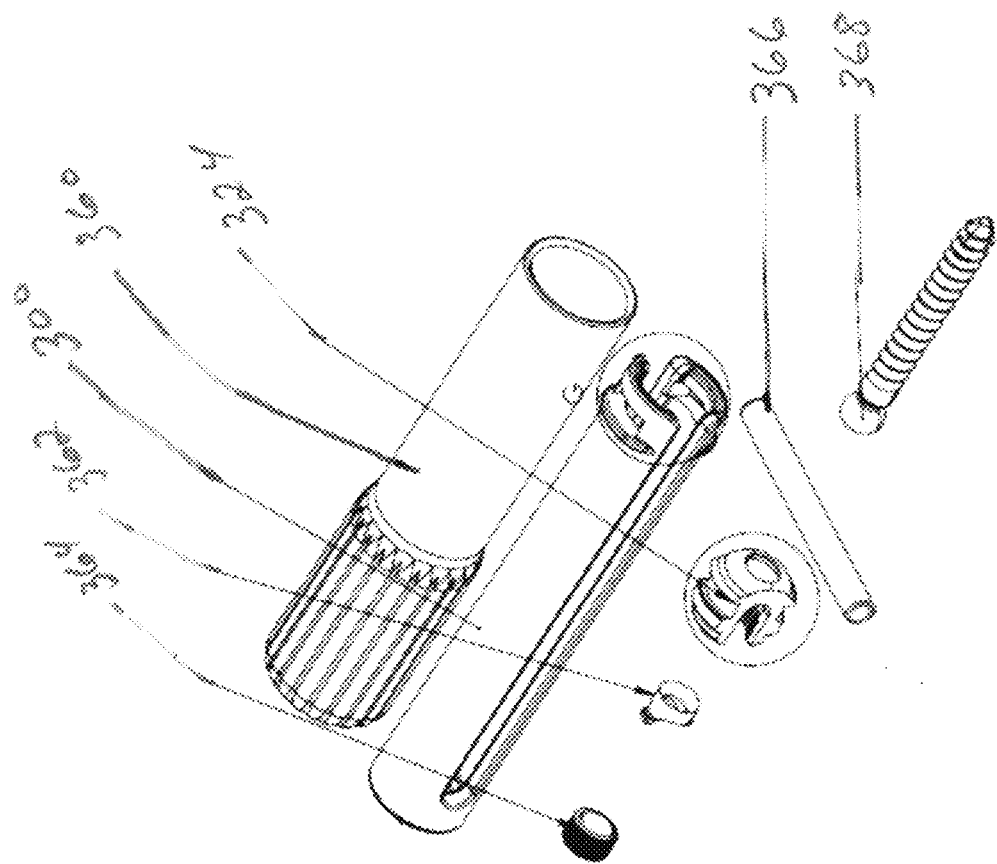
FIG. 28 is an exploded view of the snap fit tower assembly.

Referring to FIGS. 24A-24C, the pedicle screw tulip 324 is keyed or has conjugate portions that are designed to fit with and/or engage with portions of the pedicle screw engagement members 308. The pedicle screw tulip 324 has a U-shaped body 334 having a pair of slotted openings or gaps 336A and 336B sized and shaped to allow for a rod to fit and rest within, dividing the U-shaped body 334 into a right portion 338 and a left portion 340. The right portion 338 and the left portion 340 each comprise a pedicle screw tower engaging member 342. The pedicle screw tower engaging members 342 are designed to engage with and/or secure to the pedicle screw engagement members 308. The pedicle screw tower engaging members 342 include a channel or recessed portion 344 defined by an upper flanged body or protuberance 346 and a lower flanged body or protuberance 348. A bottom surface 350 of the upper flanged body or protuberance 346 forms an upper seat of the channel or recessed portion 344. An upper surface 352 of the lower flanged body or protuberance 348 forms an upper seat of the channel or recessed portion 344.

The upper flanged body or protuberance 346 is sized and shaped to fit within the pedicle screw tulip receiving portion 326 (as a slotted opening) of the pedicle screw engagement members 308. The pedicle screw tower engaging member channel or recessed portion 344 is sized and shaped to correspond with the size and shape of the pedicle screw tulip engagement area 328. When engaged, the lower flanged body or protuberance 348 rests just below the distal or bottom surface 330 of the tower pedicle screw system 300. The pedicle screw tulip 324 may further include internal threading 354 and a bottom seat opening 356 sized and shaped to receive at least a portion of a pedicle screw.

Figure 29:
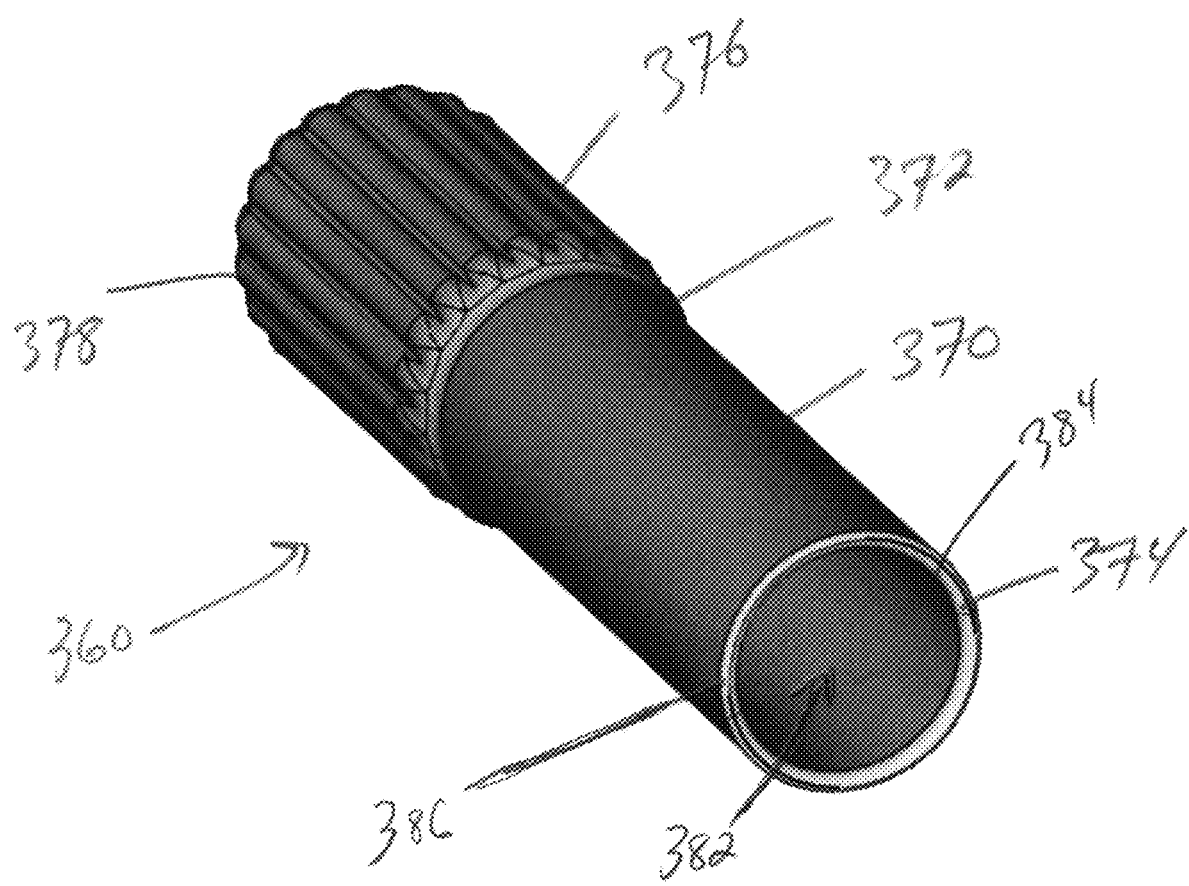
FIG. 29 is a perspective view of an illustrative embodiment of a tower locker-rod pusher.

Referring to FIGS. 25-28, an illustrative embodiment of a tower assembly, referred to as a snap fit tower assembly 358 is shown. The snap fit tower assembly 358 may include one or more, in any combination, of the tower pedicle screw system 300, the pedicle screw tulip 324, a tower locker-rod pusher or sleeve 360, a receiving screw ring or collar 362, a nut or set screw 364, a rod 366, and a screw 368, see FIGS. 27 and 28. The tower locker-rod pusher or sleeve 360 is designed to and fit over the tower pedicle screw system 300 and prevent the right side portion 314 and the left side portion 316 from opening up or displaying out, and disengaging from the pedicle screw tulip 324. Referring to FIG. 29, the tower locker-rod pusher or sleeve 360 is shown having a main body 370 having a first end 372 and a second, opposing end 374. The first end 372 may include a knob structure 376 having multiple ribs 378, and functions to aid in griping the knob structure 376. The first end 372 includes an opening 380, see FIG. 27, to allow access to the interior 382. The second end 374 includes an opening 384. The bottom surface 386 rests against the pedicle screw engagement member flanged body or protuberance 332 when the tower locker-rod pusher 360 is inserted over the tower pedicle screw system 300.

Figure 30B:
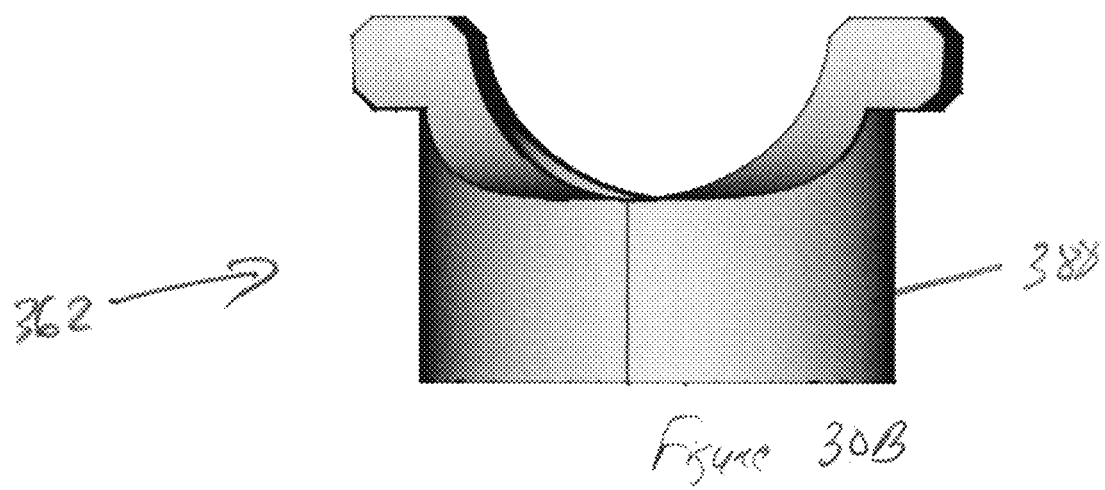
FIG. 30B is a side view of the screw ring.
Figure 30A:
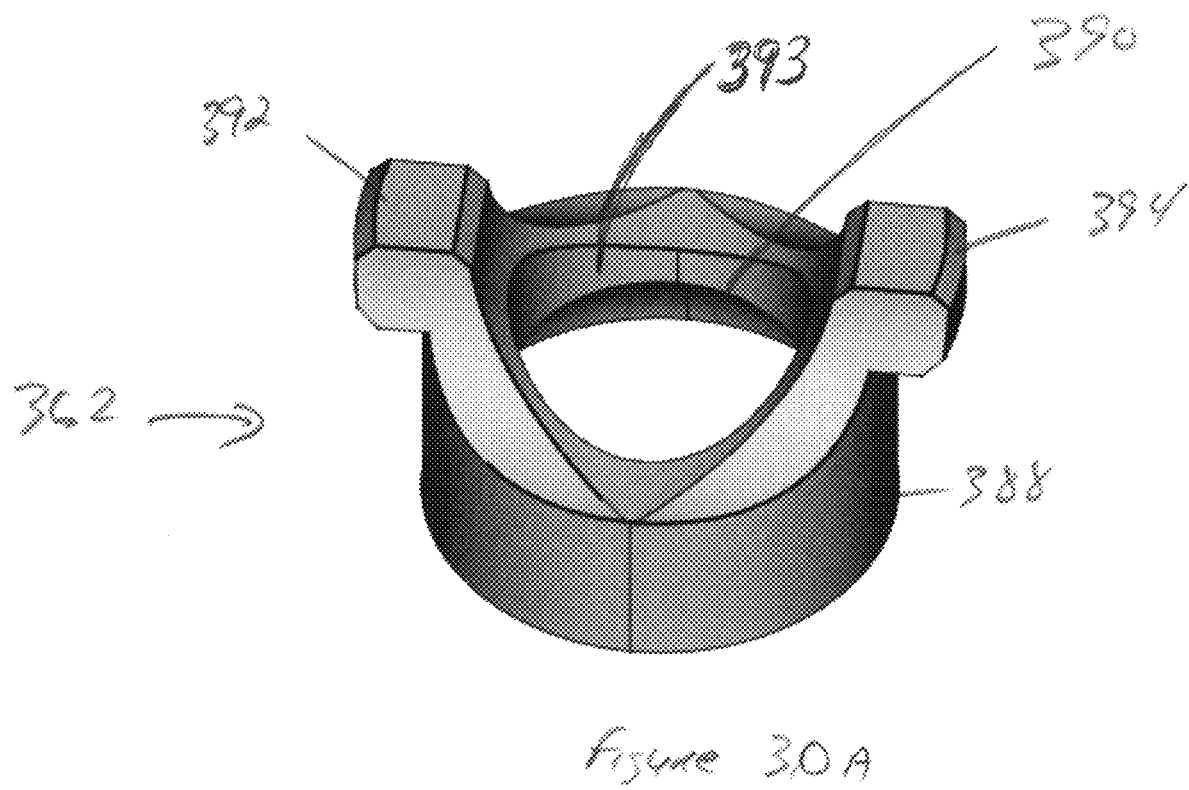
FIG. 30A is a perspective view of an illustrative embodiment of a screw ring.
Figure 34:
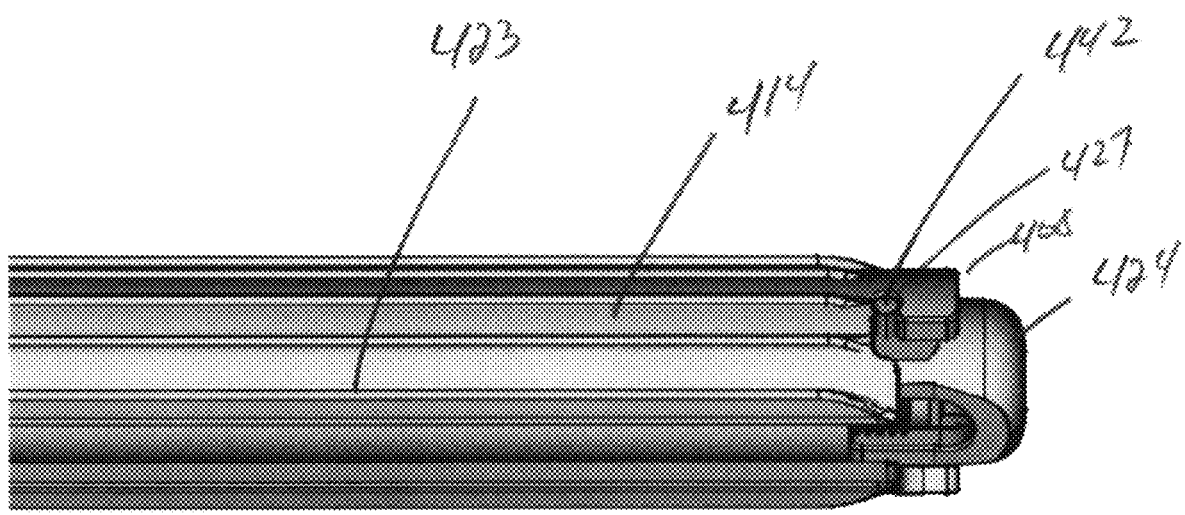
FIG. 34 illustrates the turn fit tower pedicle screw locking members secured to a keyed or conjugate pedicle screw tulip head.

Referring to FIGS. 30A-31, an illustrative embodiment of the receiving screw ring or collar 362 is shown. The receiving screw ring or collar 362 secures or screws into pedicle screw tulip 324 and functions to allow for variability of angle orientation of the pedicle screw 368, twisting to lock the pedicle screw from a polyaxial orientation to monoaxial orientation. The receiving screw ring or collar 362 includes a generally circular body 388 having a center opening 390 and cup shaped seat 393 sufficient to receive and allow a pedicle screw head to fit and/or float within. The circular body 388 includes knob structures 392 and 394 which function to secure the receiving screw ring or collar 362 to the head of pedicle screw tulip 324.

Referring to FIGS. 31-35, an illustrative example of the tower pedicle screw system with a turn fit pedicle screw locking member, referred to as tower pedicle screw system 400, is shown. The tower pedicle screw system 400 may include many of the same structural components and many of the same functions as described previously. The pedicle screw tower 400 comprises a first end 402, a second opposing end 404, and a main body 406 separating the first end 402 and the second opposing end 404. The main body 406 is shown as an elongated body, having a generally tube like shape. Secured to or integrally formed from the second end 404 is a pedicle screw engagement member 408. The pedicle screw engagement member 408 is configured to removably engage with a portion or section of a conjugate or keyed pedicle screw tulip (424, see FIG. 38). The pedicle screw tower 400 comprises a pair of longitudinal slotted openings or gaps 410, 412 running from below the first end 402 and through the second end 404 and pedicle screw engagement members 408. The longitudinal slots 410 and 412 divide the main body 406 into a right side portion 414 and a left side portion 416. The right side portion 414 includes a pedicle screw engagement member 408. The left side portion 416 includes a pedicle screw engagement member 408.

The first end 402 may terminate in an opening 418, allowing other medical devices or equipment to be inserted and move within an interior or inner lumen 420. The interior or inner lumen 420 is defined by an inner surface 422. By having the longitudinal slits or openings 410, 412 extend below the first end 402, partial flexibility may be imparted on the right side portion 414 and the left side portion 416. In this case, the right side portion 414 or the left side portion 416 may be movable away from or towards the center of the main body 406 if a force is applied. The pedicle screw tower 400 may be made of a material that allows the right side portion 414 or the left side portion 416 to snap or move back to its original position once the force is removed. While illustrated with an opening 418, the pedicle screw tower 400 may also have a closed end. In addition, the main body 406 may not have longitudinal slits 410 and/or 412. The main body 406 is also shown having longitudinal fins 423. The longitudinal fins 423 extend from the first end 402 to the pedicle screw engagement member 408 and define a groove or channel 425. The groove or channel 425 may have a curvilinear shape to mirror the shape of a curvilinear retractor blade and provide retractor functionality. While the figures illustrate multiple fins 423 and grooves or channels 425, the main body may include two fins 423 forming a single groove or channel 425 per side (414 and 416). The longitudinal fins 423 may be configured not to extend the entire distance from the first end 402 to the pedicle screw engagement member 408.

The pedicle screw engagement member(s) 408 is configured to provide engagement with the pedicle screw tulip 424. The pedicle screw engagement member 408 is shown having a pedicle screw tulip receiving portion 426, illustrated herein as a curved slotted opening. The pedicle screw tulip receiving portion 426 is sized and shaped to receive and hold therein at least a portion of the pedicle screw tulip 424. The pedicle screw tulip receiving portion 426 may assume a bent finger like shape ending in a rounded or partially circular shaped surface 427. The pedicle screw engagement member 408 may also include a foot like appendage 428 having a side curved surface 430 and a bottom surface 432, which may be linear or partially curved.

Figure 38:
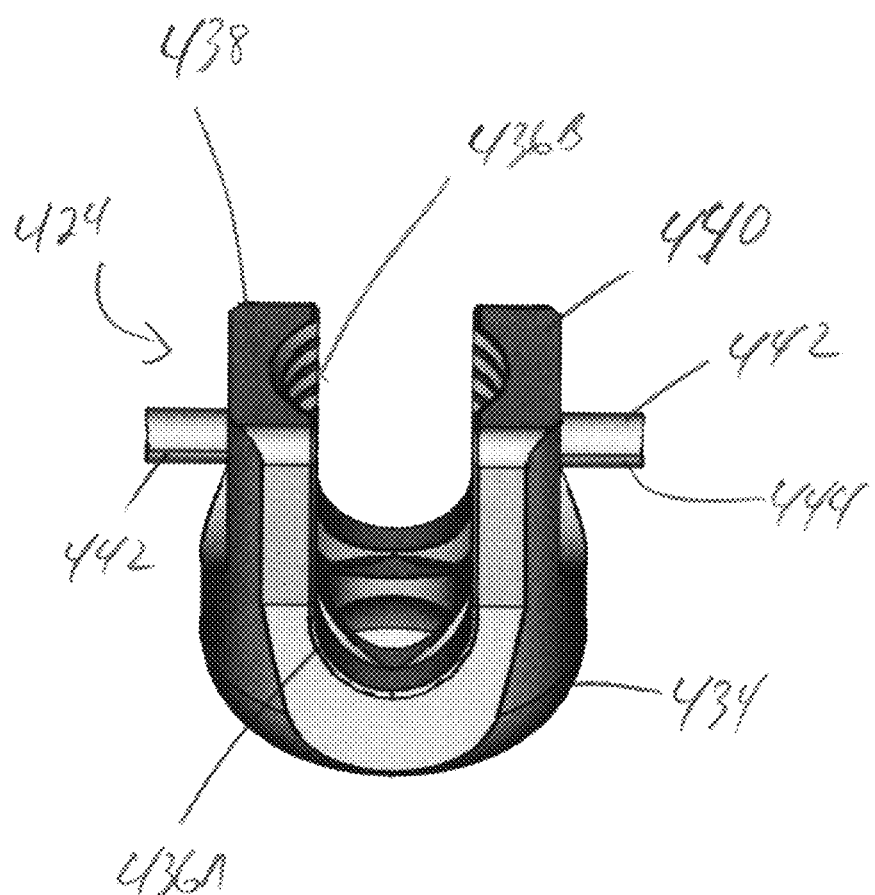
FIG. 38 is a perspective view of the keyed or conjugate turn fit pedicle screw tulip head.

Referring to FIG. 38, the pedicle screw tulip 424 is keyed or has conjugate portions that are designed to fit with and/or engage with portions of the pedicle screw engagement member(s) 408. The pedicle screw tulip 424 has a U-shaped body 434 having a pair of slots 436A and 436B sized and shaped to allow for a rod to fit and rest within, dividing the U-shaped body 434 into a right portion 438 and a left portion 440. The right portion 438 and the left portion 440 each comprise a pedicle screw tower engaging member 442. The pedicle screw tower engaging member 442 is designed to engage with and/or secure to the pedicle screw engagement member 408. The pedicle screw tower engaging member 442 includes an elongated body 444, illustrated as a rod, extending out and away from the U-shaped body 434. The elongated body 444 is designed to contact the first surface 446 of the pedicle screw tulip receiving portion 426. The first surface 446 guides the elongated body 444 as it is slid upwardly and over towards a second surface 448, eventually locking in place within the rounded or partially circular shaped surface 427, see also FIG. 34.

Figure 35:
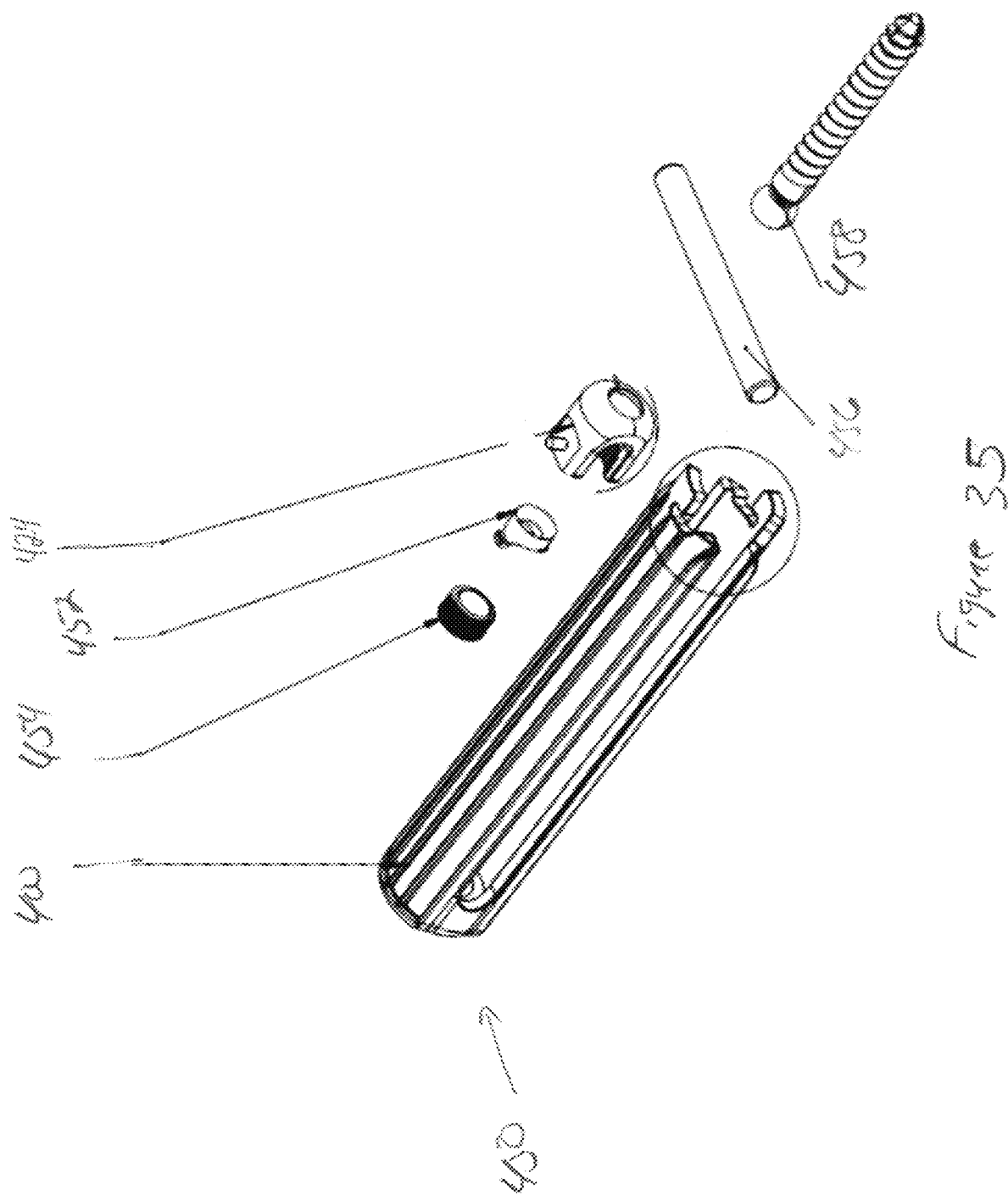
FIG. 35 is an exploded view of the turn fit tower assembly.
Figure 36:
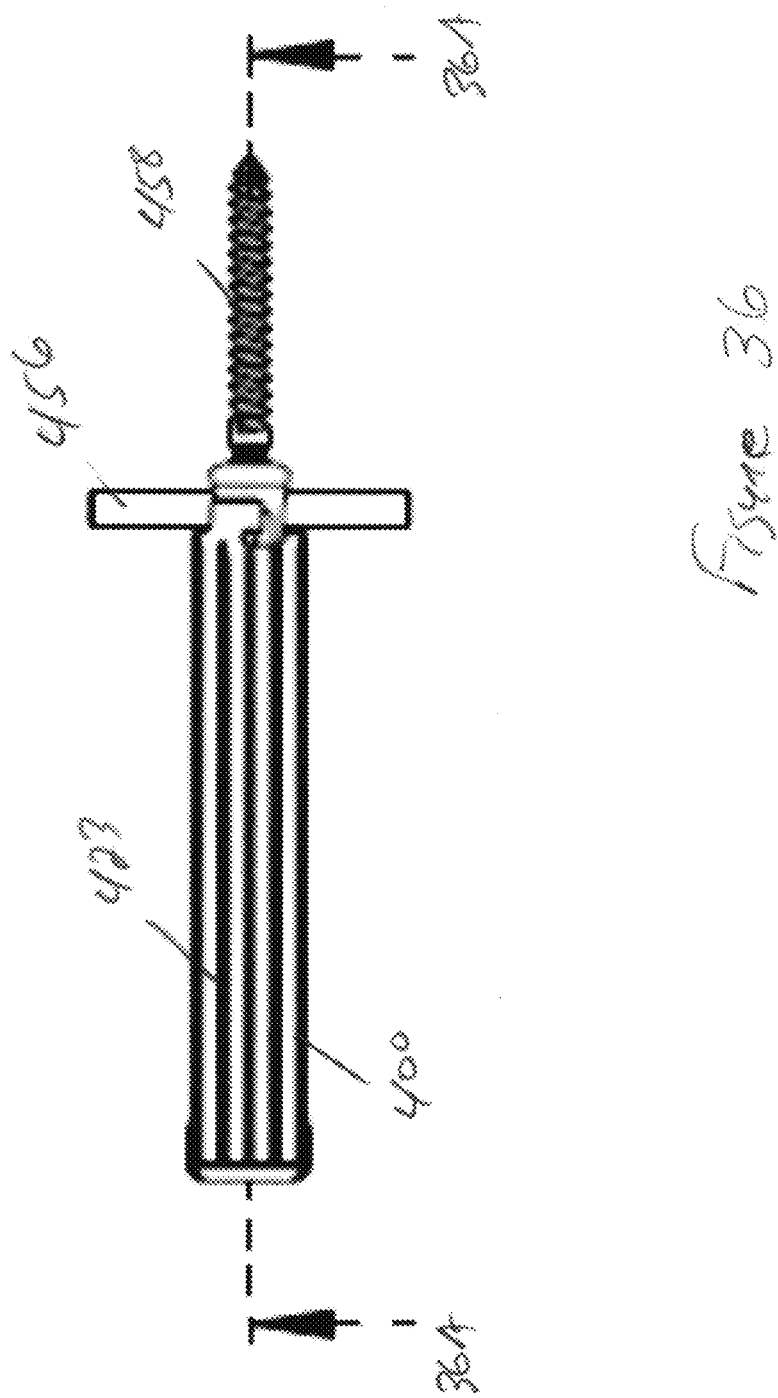
FIG. 36 is a side view of the turn fit tower assembly.
Figure 37:
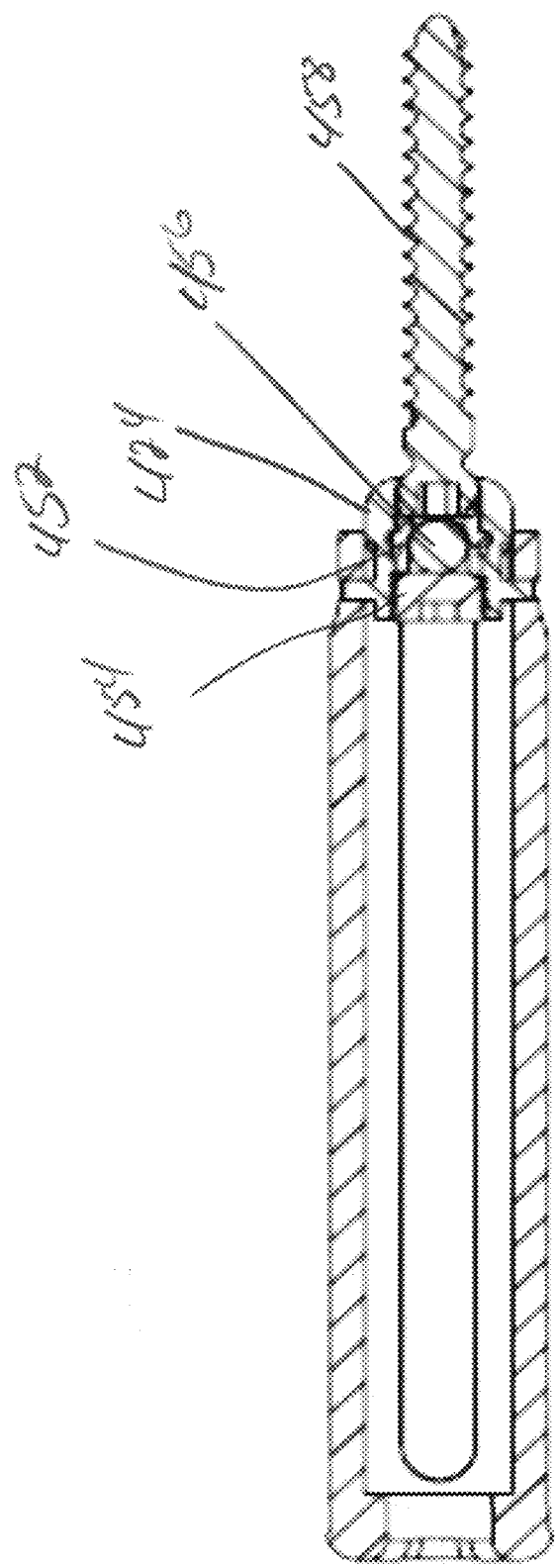
FIG. 37 is a cross-sectional view of the snap fit tower assembly taken along lines 36A-36A of FIG. 36.

Referring to FIGS. 35-37, an illustrative embodiment of a tower assembly, referred to as a turn fit tower assembly 450 is shown. The turn fit tower assembly 450 may include one or more, in any combination, of the tower pedicle screw system 400, the pedicle screw tulip 424, a receiving screw ring or collar 452 (same as receiving screw ring or collar 362), a threaded nut or set screw 454, a rod 456, and a threaded screw 458.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A screw tower for use in medical procedures comprising:
   a first end;
   a second end;
   a main body separating said first end and said second end by a length, said main body comprising a first elongated member and a second elongated member, said first elongated member and said second elongated member separated by a space and connecting at said first end by a first end surface, said space defining an interior region;
   a first surgical screw engagement member configured to removably engage with an outer surface of a first side of a surgical screw tulip, said first surgical screw engagement member comprising an exterior surface, an interior surface having a curvature shaped to mirror a curvature of said surgical screw tulip it engages with, and a first surgical screw locking member, said first surgical screw locking member comprising a first wall, a second opposing wall, a closed end, and an open end defined by a space separating said first wall and said second wall, said first wall, said second wall, and said closed end are arranged to define a first surgical screw locking member interior, said first surgical screw locking member interior sized and shaped to receive and secure to a conjugate or keyed shaped tower engagement member positioned on said outer surface of said first side of said surgical screw tulip; and
   a second surgical screw engagement member configured to removably engage with an outer surface of a second side of said surgical screw tulip, said second surgical screw engagement member comprising an exterior surface, an interior surface having a curvature shaped to mirror a curvature of said surgical screw tulip it engages with, and a second surgical screw locking member, said second surgical screw locking member comprising a first wall, a second opposing wall, a closed end, and an open end defined by a space separating said first wall and said second wall, said first wall, said second opposing wall, and said closed end are arranged to define a second surgical screw locking member interior, said second surgical screw locking member interior sized and shaped to receive and secure to a conjugate or keyed shaped tower engagement member positioned on said outer surface of said second side of said surgical screw tulip,
   wherein, when engaging with said surgical screw tulip, rotation of said main body in one direction causes said first surgical screw locking member to engage with said tower engagement member positioned on said first side of said surgical screw tulip simultaneously as said second surgical screw locking member engages with said tower engagement member positioned on said second side of said surgical screw tulip, and rotation of said main body in an opposite direction causes said first surgical screw locking member to disengage with said tower engagement member positioned on said first side of said surgical screw tulip simultaneously as said second surgical screw locking member disengages with said tower engagement member positioned on said second side of said surgical screw tulip.

2. The screw tower for use in medical procedures according to claim 1, wherein said first surgical screw locking member and said second surgical screw locking member are arranged about 180 degrees opposite each other.

3. The screw tower for use in medical procedures according to claim 1, wherein said main body is constructed and arranged to be height adjustable.

4. The screw tower for use in medical procedures according to claim 3, wherein,
   said main body first elongated member comprises two segments, wherein one segment is constructed and arranged to move within a second segment to provide height adjustment of said first elongated member; and
   said main body second elongated member comprises two segments, wherein one segment is constructed and arranged to move within a second segment to provide height adjustment of said second elongated member.

5. The screw tower for use in medical procedures according to claim 1, further including a tower-tulip locking mechanism constructed and arranged to prevent separation of said first surgical screw engagement member or said second surgical screw engagement member from said surgical screw tulip when attached thereto during a procedure.

6. The screw tower for use in medical procedures according to claim 5, wherein said tower-tulip locking mechanism includes a collar.

7. The screw tower for use in medical procedures according to claim 5, wherein said tower-tulip locking mechanism includes a wire running along the length of said surgical screw tower main body and a locking pin.

8. The screw tower for use in medical procedures according to claim 7, wherein said wire is operatively coupled to an actuating device, which, when rotated, moves said locking pin in a linear direction.

9. The screw tower for use in medical procedures according to claim 1, wherein said first end surface comprises an opening.

10. The screw tower for use in medical procedures according to claim 1, wherein said first elongated member and said second elongated member are moveable away from or towards a longitudinal axis of said main body when a force is applied or removed.

11. The screw tower for use in medical procedures according to claim 1, wherein,
    said first surgical screw locking member comprises a secondary surgical screw locking member, said first surgical screw engagement member secondary locking member comprising a cut-out section within said first wall, said cut out section sized and shaped to receive and secure to said conjugate or keyed shaped tower engagement member positioned on said outer surface of said first side of said surgical screw tulip; and
    said second surgical screw locking member comprises a secondary locking mechanism, said second surgical screw engagement member secondary locking mechanism comprising a cut-out section within said first wall, said cut out section sized and shaped to receive and secure to said conjugate or keyed shaped tower engagement member positioned on said outer surface of said second side of said surgical screw tulip.

12. The screw tower for use in medical procedures according to claim 1, wherein said first surgical screw locking member interior is sized and shaped to receive an elongated object located on said outer surface of said first side of said surgical screw tulip; and said second surgical screw locking member interior is sized and shaped to receive an elongated object located on said outer surface of said second side of said surgical screw tulip.

13. The screw tower for use in medical procedures according to claim 1, wherein said first a surgical screw locking member interior is sized and shaped to receive a cylindrical or rod shaped object extending away from said outer surface of said first side of said surgical screw tulip; and said second pedicle screw locking member interior is sized and shaped to receive a cylindrical or rod shaped object extending away from said outer surface of said second side of said surgical screw tulip.

14. The screw tower for use in medical procedures according to claim 1, wherein said main body includes one or more longitudinal fins.

15. The screw tower for use in medical procedures according to claim 14, wherein said one or more longitudinal fins extend along an entire length of said main body.

16. The screw tower for use in medical procedures according to claim 14, wherein said one or more longitudinal fins extend along a length which is less than an entire length of said main body.

17. The screw tower for use in medical procedures according to claim 1, wherein said main body includes one or more longitudinal fins and one or more channels.

18. The screw tower for use in medical procedures according to claim 1, further including an outer sleeve constructed and arranged to fit over said main body.

19. The screw tower for use in medical procedures according to claim 1, wherein said surgical screw is a pedicle screw and said surgical screw tulip is a pedicle screw tulip.

20. The screw tower for use in medical procedures according to claim 1, wherein said surgical screw is a lateral mass screw and said surgical screw tulip is a lateral mass screw tulip.

* * * * *